(12) United States Patent
Calton et al.

(10) Patent No.: US 7,628,793 B2
(45) Date of Patent: Dec. 8, 2009

(54) KNEE BALANCING BLOCK

(75) Inventors: Thomas F. Calton, Ogden, UT (US);
Matthew M. Lowe, Draper, UT (US);
Michael D. Ensign, Draper, UT (US);
Scott Shaver, Broomfield, CO (US)

(73) Assignee: Ortho Development Corporation, Draper, UT (US)

( * ) Notice: Subject to any disclaimer, the term of this patent is extended or adjusted under 35 U.S.C. 154(b) by 1148 days.

(21) Appl. No.: 10/618,521

(22) Filed: Jul. 11, 2003

(65) Prior Publication Data
US 2005/0049603 A1 Mar. 3, 2005

Related U.S. Application Data

(60) Provisional application No. 60/398,289, filed on Jul. 23, 2002, provisional application No. 60/474,454, filed on May 30, 2003.

(51) Int. Cl.
*A61B 17/58* (2006.01)
(52) U.S. Cl. ........................................................ 606/88
(58) Field of Classification Search .................. 606/79, 606/86, 87, 88, 96, 89, 86 R; 623/20.14, 623/20.35
See application file for complete search history.

(56) References Cited

U.S. PATENT DOCUMENTS

| | | | | |
|---|---|---|---|---|
| 4,457,307 A | * | 7/1984 | Stillwell | 606/88 |
| 4,566,448 A | * | 1/1986 | Rohr, Jr. | 606/88 |
| 4,646,729 A | | 3/1987 | Kenna et al. | |
| 4,653,488 A | | 3/1987 | Kenna | |
| 4,703,751 A | * | 11/1987 | Pohl | 606/62 |
| 4,787,383 A | | 11/1988 | Kenna | |
| 4,825,857 A | | 5/1989 | Kenna | |
| 4,841,975 A | | 6/1989 | Woolson | |
| 4,952,213 A | * | 8/1990 | Bowman et al. | 606/79 |
| 5,067,898 A | * | 11/1991 | Dury | 433/75 |
| 5,122,144 A | * | 6/1992 | Bert et al. | 606/88 |
| 5,234,433 A | | 8/1993 | Bert et al. | |
| 5,342,367 A | | 8/1994 | Ferrante et al. | |
| 5,364,401 A | | 11/1994 | Ferrante et al. | |
| 5,417,694 A | | 5/1995 | Marik et al. | |

(Continued)

OTHER PUBLICATIONS

Calton, Thomas F., M.D. "Total Knee Arthroplasty BKS Experience." Oct. 2003, Ogden, Utah. Presented in Japan.*

*Primary Examiner*—Thomas C Barrett
*Assistant Examiner*—James L. Swiger
(74) *Attorney, Agent, or Firm*—Matthew D. Thayne; Stoel Rives LLP

(57) ABSTRACT

An orthopedic A/P cutting guide device, including a cut guide member, a support member and a positioning member for permitting both (i) rotational, and (ii) translational movement after the A/P cutting guide device has been attached to the distal femur by quick pins or other securing devices, is disclosed. Rotational movement may occur by loosening a knob thereby releasing the positioning member and the cut guide member from the support member, which may be fixed in position by the quick pins, and rotating the positioning member and the cut guide member together. Translational movement may occur by loosening a plurality of knobs thereby releasing the cut guide member from the support member and the positioning member, and moving the cut guide member anteriorly or posteriorly. After the device has been rotated and translated, the knobs may be tightened, thus securing the device from further movement.

40 Claims, 14 Drawing Sheets

U.S. PATENT DOCUMENTS

| | | | |
|---|---|---|---|
| 5,423,827 A * | 6/1995 | Mumme et al. | 606/96 |
| 5,464,406 A | 11/1995 | Ritter et al. | |
| 5,486,178 A * | 1/1996 | Hodge | 606/82 |
| 5,514,139 A | 5/1996 | Goldstein et al. | |
| 5,514,140 A | 5/1996 | Lackey | |
| 5,540,696 A | 7/1996 | Booth, Jr. et al. | |
| 5,562,675 A * | 10/1996 | McNulty et al. | 606/96 |
| 5,597,379 A | 1/1997 | Haines et al. | |
| 5,611,802 A | 3/1997 | Samuelson et al. | |
| 5,624,444 A | 4/1997 | Wixon et al. | |
| 5,643,272 A | 7/1997 | Haines et al. | |
| 5,649,929 A | 7/1997 | Callaway | |
| 5,662,656 A * | 9/1997 | White | 606/88 |
| 5,683,397 A | 11/1997 | Vendrely et al. | |
| 5,688,280 A | 11/1997 | Booth, Jr. et al. | |
| 5,688,282 A | 11/1997 | Baron et al. | |
| 5,735,856 A | 4/1998 | McCue et al. | |
| 5,749,876 A | 5/1998 | Duvillier et al. | |
| 5,810,827 A | 9/1998 | Haines et al. | |
| 5,810,831 A | 9/1998 | D'Antonio | |
| 5,830,216 A * | 11/1998 | Insall et al. | 606/88 |
| 5,911,723 A | 6/1999 | Ashby et al. | |
| 5,925,049 A | 7/1999 | Gustilo et al. | |
| 5,938,665 A | 8/1999 | Martin | |
| 6,013,081 A | 1/2000 | Burkinshaw et al. | |
| 6,024,746 A | 2/2000 | Katz | |
| 6,056,754 A | 5/2000 | Haines et al. | |
| 6,059,788 A | 5/2000 | Katz | |
| 6,077,270 A | 6/2000 | Katz | |
| 6,258,096 B1 | 7/2001 | Seki | |
| 6,290,704 B1 | 9/2001 | Burkinshaw et al. | |
| 6,296,646 B1 | 10/2001 | Williamson | |
| 6,458,135 B1 | 10/2002 | Harwin et al. | |
| 6,478,799 B1 | 11/2002 | Williamson | |
| 6,602,258 B1 | 8/2003 | Katz | |
| 7,029,477 B2 * | 4/2006 | Grimm | 606/88 |

* cited by examiner

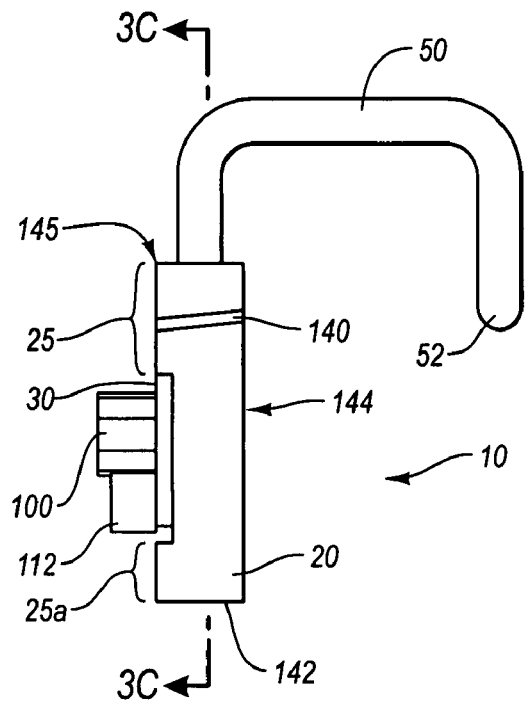
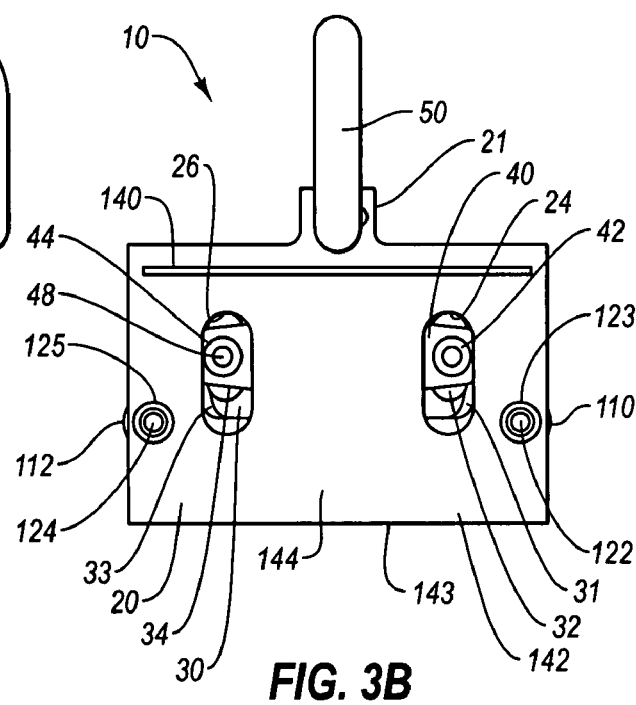
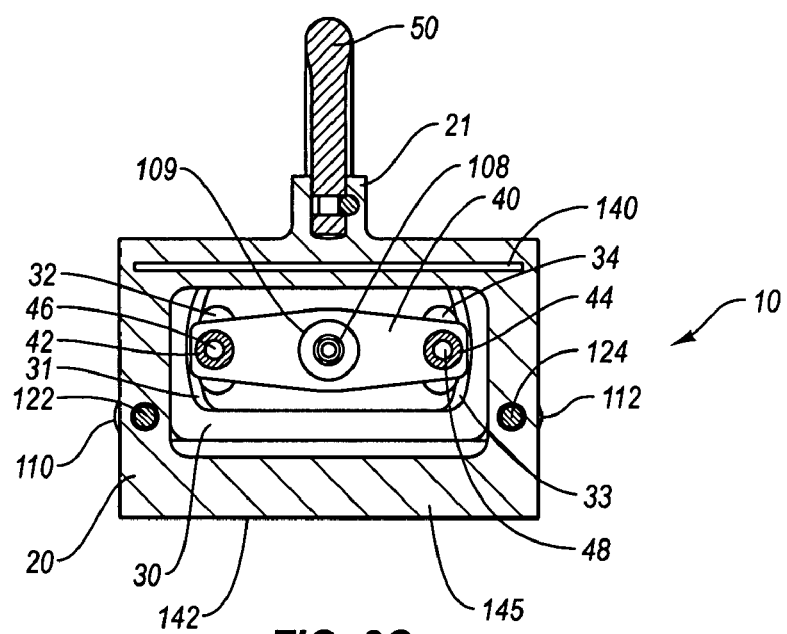
FIG. 3A
FIG. 3B
FIG. 3C

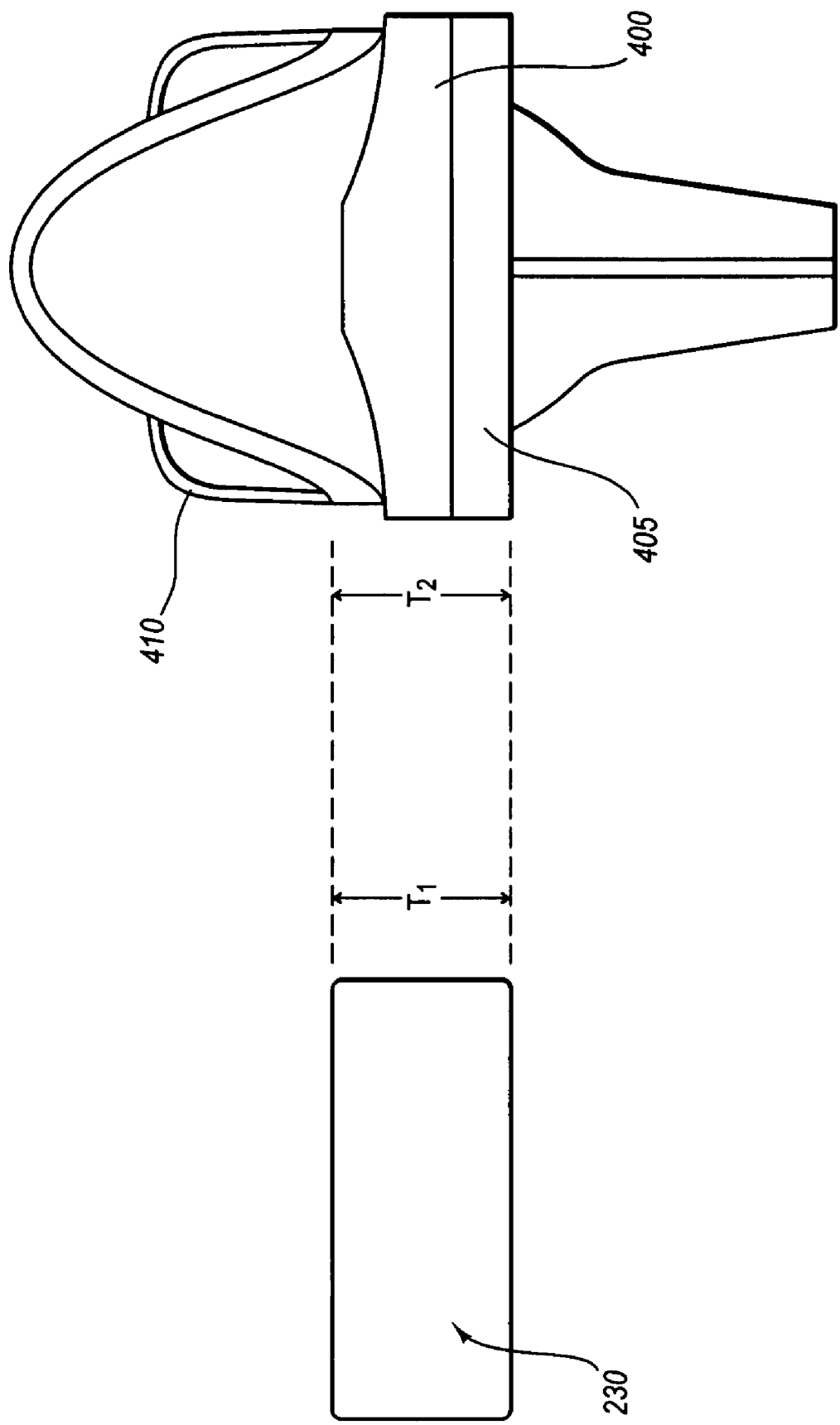

KNEE BALANCING BLOCK

CROSS-REFERENCE TO RELATED APPLICATIONS

This application claims the benefit of U.S. Provisional Application No. 60/398,289, filed Jul. 23, 2002, and U.S. Provisional Application No. 60/474,454 filed May 30, 2003, which are hereby incorporated by reference herein in their entireties, including but not limited to those portions that specifically appear hereinafter, the incorporation by reference being made with the following exception: In the event that any portion of either of the above-referenced applications is inconsistent with this application, this application supercedes said portion of said above-referenced applications.

STATEMENT REGARDING FEDERALLY SPONSORED RESEARCH OR DEVELOPMENT

Not Applicable.

BACKGROUND OF THE INVENTION

1. The Field of the Invention

The present invention relates generally to orthopedic surgical devices, and more particularly, but not necessarily entirely, to a device and method for balancing flexion and extension gaps in total knee replacement surgery, and for preparing the knee joint, to receive an implant.

2. Description of Related Art

The knee joint is comprised essentially of four bones, the fibula, the tibia, the femur, and the patella or knee cap. The two major bones, namely the proximal portion of the tibia and the distal portion of the femur, articulate with one another forming the main articulation surface of the knee joint. More specifically, articulation between each condyle of the distal femur and the corresponding meniscus and condyle of the proximal tibia permits positioning of a patient's leg in both flexion and extension.

When a knee joint is damaged such that total knee arthroplasty (TKA) is required, resection of the proximal portion of the tibia and the distal portion of the femur is required to form an extension gap between said proximal portion of the tibia and said distal portion of the femur when the patient's leg is in full extension. Additionally, a posterior resection of the distal femur is required to form a flexion gap between said proximal portion of the tibia and said distal portion of the femur when the patient's leg is in full flexion. In creating the extension and flexion gaps it is advantageous to resect the bones in such a manner so as to form equivalent rectangular gaps between the proximal portion of the tibia and the distal portion of the femur when the patient's leg is fully extended and flexed. In other words, each gap may be defined by cuts made in the proximal tibia and the distal femur that are substantially parallel to one another creating two rectangular gaps that are substantially equivalent. It will be appreciated that a width of the extension gap may be substantially equivalent to a width of the flexion gap. These substantially equivalent rectangular gaps aid in creating the balance in the knee that will ultimately allow the patient to both fully flex and extend the leg.

In classic technique knee surgeries, the first portion of the surgery is usually the same, which essentially requires a surgeon to prepare the knee joint in a manner so as to create the extension gap. The extension gap may be formed by making a distal cut in the femur using a distal cut guide to prepare the femur for further operative steps. It will be appreciated that this first portion of the surgery comprises several individual steps, which will be expounded upon hereinafter in more detail. Each step aids in the placement of the distal cut guide on the distal femur to create an accurate distal cut. The next portion of the surgery comprises making a proximal cut on the tibia after which the challenge becomes to create substantially equivalent rectangular extension and flexion gaps. It will be appreciated that additional surgical steps must be taken to implant the artificial knee joint and to complete the surgery, which steps will not be fully addressed herein.

It will be appreciated that in classic technique knee surgeries, used to balance and prepare the knee joint to receive the prosthetic knee implant, the major steps of the procedure include the following: First, the distal femur is cut at a valgus angle, which is defined as the angle between the neutral mechanical axis of the limb and the anatomical axis of the femur, consistent with the valgus angle of the patient. Second, the proximal tibia is cut substantially perpendicular to the long axis of the tibia. Third, the ligaments are balanced while the knee joint is in extension so that there is a substantially rectangular extension space or gap. Fourth, the femur is sized based on the anterior and posterior dimensions of the distal femur using an A/P sizing guide. The A/P sizing guide is placed on the distal femur by inserting two pins into the distal femur, attaching the A/P sizing guide to the distal femur. Fifth, the A/P sizing guide is removed from the pins, and an A/P cutting block is then positioned over the pins and onto the distal femur. Sixth, the posterior cut is made in the distal femur, and the A/P cutting block and the pins are removed from the bone. Seventh, a spacer block is used to determine the equality of the flexion and extension gaps. Eighth, the remaining cuts are finished, and then a trial reduction is performed.

It will be appreciated that the above surgical procedure is merely one example of the many techniques that have been used in the orthopedic industry for knee replacement surgeries. It will be further appreciated that the above surgical procedure is not meant to be exhaustive, or even a summary, of the many surgical techniques that are used in the orthopedic industry to perform total knee replacement surgeries.

With many of the prior art knee balancing devices used in total knee replacement surgeries, positioning of the knee balancing device depends entirely on the placement of the pins in the distal femur. Such pin placement requires great precision in order to properly place and locate the knee balancing device on the femur. If the pins are not properly placed, the device will be mal-aligned on the distal femur. The surgeon must then remove at least one of the pins from the distal femur, and re-secure the at least one pin to the bone for another attempt at securing the knee balancing device to the bone in an aligned position, which drastically increases the time and difficulty of the surgery. The prior art knee balancing devices may also lead to over resection of the bones in the knee joint, as substantially equivalent rectangular gaps are sought, which may potentially cause problems if a later revision surgery becomes necessary.

Attempts have been made in the prior art to provide a device and method for locating the A/P cutting guide on the distal femur such that the device may be correctly placed and located on the distal femur initially, without the necessity of removing the device and re-pinning the device to the bone. For example, U.S. Pat. No. 5,364,401 (granted Nov. 15, 1994 to Ferrante et al.) discloses a system for resecting the distal femur where various devices can be sequentially placed on a base member having a pair of connected brackets that are axially and radially adjustable after being initially positioned on the bone. During a final stage of bone preparation, the system utilizes a cutting block that may be adjusted relative to its base. This device is characterized by several disadvantages, including the need to connect a complex series of brackets to a base creating a scaffolding to which several devices may be removably attached.

U.S. Pat. No. 5,830,216 (granted Nov. 3, 1998 to Insall et al.) discloses a set of instruments for orientation of the femoral implant, including an epicondylar guide configured for referencing external rotation from the epicondyles. The Insall et al. patent further discloses a posterior reference/rotation guide that can be attached to the epicondylar guide for checking the rotation relative to the intact posterior condyles to confirm the epicondylar setting, and an A/P cutting guide comprising a fin that is designed to fit into a slot cut in the distal femur so as to fix external rotation. The A/P cutting guide can only move in the anterior and posterior directions for making adjustments in the flexion and extension gaps. This device is disadvantageous because there is no mechanism for adjusting the rotation of the A/P cutting guide, making each step in the surgery crucial, leaving little to no room for human error.

The present invention is directed to an orthopedic device for flexion and extension balancing in the knee joint by creating substantially equivalent rectangular flexion and extension gaps between the patient's proximal tibia and distal femur. It is noteworthy that none of the prior art known to applicants provides an A/P cutting guide device that is easy to operate, has few component parts and a relatively low profile, and that may be adjusted (i) translationally, in the anterior and posterior directions relative to at least one pin placed in the distal femur, and (ii) rotationally, relative to the at least one pin placed in the distal femur, to which the A/P cutting guide may be attached.

The prior art is thus characterized by several disadvantages that are addressed by the present invention. The present invention minimizes, and in some aspects eliminates, the above-mentioned failures, and other problems, by utilizing the methods and structural features described herein.

The features and advantages of the invention will be set forth in the description which follows, and in part will be apparent from the description, or may be learned by the practice of the invention without undue experimentation. The features and advantages of the invention may be realized and obtained by means of the instruments and combinations particularly pointed out herein and in the appended claims.

BRIEF DESCRIPTION OF THE DRAWINGS

The features and advantages of the invention will become apparent from a consideration of the subsequent detailed description presented in connection with the accompanying drawings in which:

FIG. 3A is a side view of the A/P cutting guide device of FIG. 3, made in accordance with the principles of the present invention;

FIG. 3B is a back view of the A/P cutting guide device of FIG. 3, made in accordance with the principles of the present invention;

FIG. 3C is a cross-sectional view of the A/P cutting guide device taken along the line A-A of FIG. 3A;

FIG. 19 is a front view of the spacer block in relation to a tibial polyethylene insert, a tibial tray, and a femoral component.

DETAILED DESCRIPTION OF THE INVENTION

Figure 1:
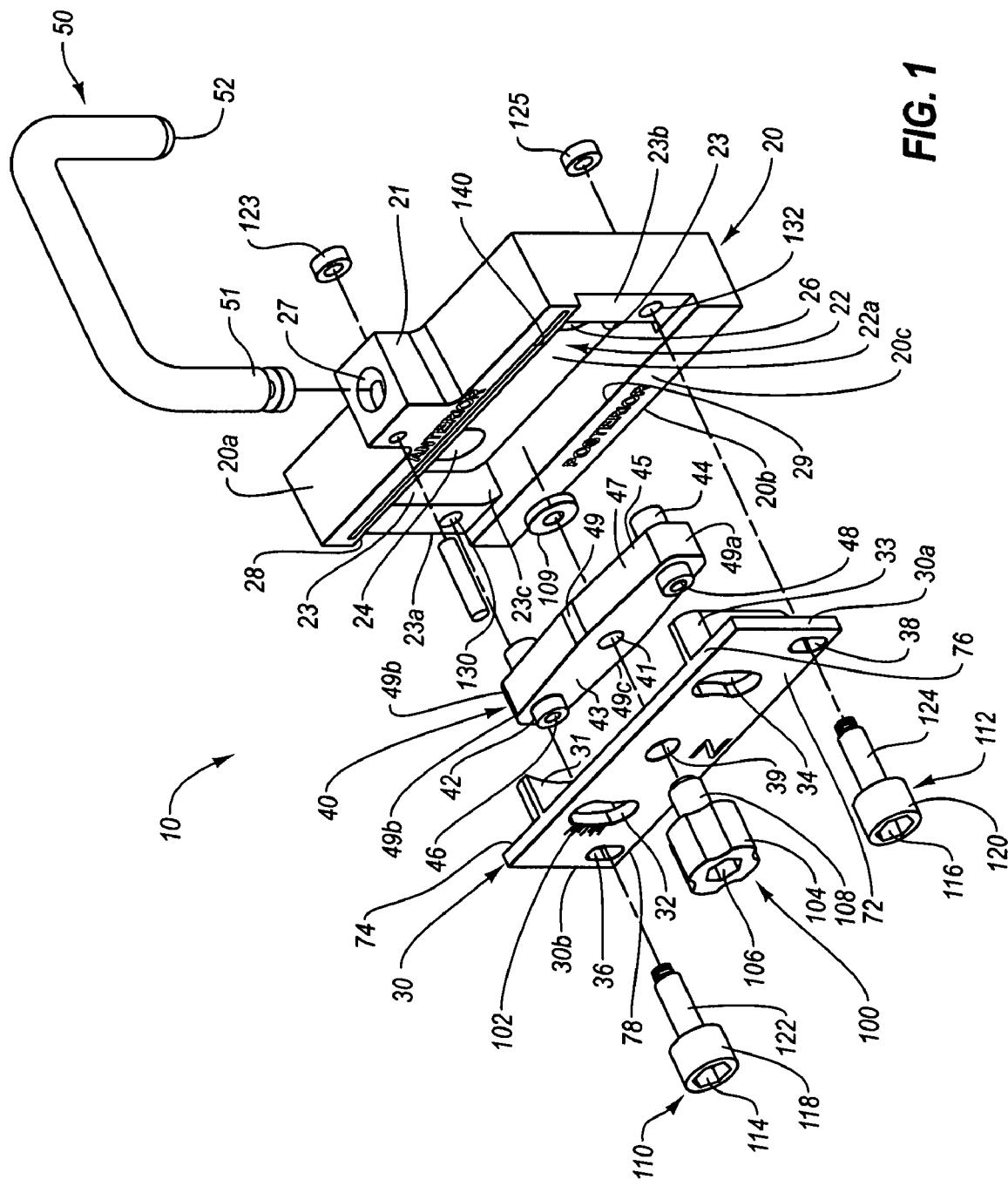
FIG. 1 is an exploded perspective view of an A/P cutting guide device illustrating a cut guide member, a support member, and a positioning member made in accordance with the principles of the present invention.

For the purposes of promoting an understanding of the principles in accordance with the invention, reference will now be made to the embodiments illustrated in the drawings and specific language will be used to describe the same. It will nevertheless be understood that no limitation of the scope of the invention is thereby intended. Any alterations and further modifications of the inventive features illustrated herein, and any additional applications of the principles of the invention as illustrated herein, which would normally occur to one skilled in the relevant art and having possession of this disclosure, are to be considered within the scope of the invention claimed.

Applicants have discovered that a total knee arthroplasty (TKA) is greatly enhanced by utilizing a unique A/P cutting guide device 10 that may be moved in both a rotational and translational manner with respect to a distal end of a femur after the A/P cutting guide device 10 has been secured, or pinned, to the distal femur. Applicants have thus conceived of a method for utilizing the unique A/P cutting guide device 10 during TKA surgeries.

The A/P cutting guide device 10 of the present invention may be configured and dimensioned to be placed on a substantially flat, previously resected distal femur. It should be noted that the A/P cutting guide device 10 will be particularly described herein in conjunction with the knee joint and particularly for resecting a posterior portion of the distal femur.

In classic technique knee replacement surgery, the first part of the surgery is essentially the same, and requires a surgeon to make two preliminary cuts, one cut on the distal femur and the other cut on the proximal tibia. It will be appreciated that the distal femoral cut may be made prior to the proximal tibial cut, or vice-versa, without departing from the scope of the present invention. Therefore, while the present invention may be described herein performing the distal femoral cut before the proximal tibial cut, it will be appreciated that such a sequence is not required.

It will further be appreciated that each cut requires several individual steps to accomplish the result, wherein the first cut results in a resection of the distal most portion of the femur, or a resection of both femoral condyles, creating a substantially flat, resected surface on the distal femur. A similar procedure performed on the proximal tibia results in the resection of the proximal most portion of the tibia, or a resection of the tibial plateau, creating a substantially flat, resected surface on the proximal tibia. After the distal femoral cut and the proximal tibial cut have each been made, a gap is formed between the cut portions of the distal femur and proximal tibia. When the knee is fully extended, this gap may be referred to as an extension gap 16 (illustrated best in FIG. 18). Soft tissue releases are then performed to make a substantially rectangular gap. When the knee is flexed, a gap created between the posterior portion of the distal femur and the proximal tibia may be referred to as a flexion gap 18 (illustrated best in FIG. 17). It is advantageous for the surgeon to create substantially parallel femoral and tibial cuts such that the extension and flexion gaps 16, 18 are each substantially equivalent and rectangular in shape.

Referring now to the device 10 of the present invention, FIG. 1 illustrates the A/P cutting guide device, generally referred to as item 10, in an exploded, perspective view. It will be appreciated that the A/P cutting guide device 10 may generally comprise a cut guide member 20, a positioning member 30, for example a positioning plate as illustrated in FIG. 1, a support member 40, and a boom 50. Each of the above components will be described herein in more detail below. It should be noted that the above components may be manufactured from martistic grade stainless steel, or any suitable biocompatible material that has been developed for manufacturing surgical instruments and tools. For example, other materials that exhibit similar strength properties to stainless steel may be used to manufacture the above components so long as the materials may be developed and manufactured into surgical instruments and tools.

It should be noted at the outset that after the initial distal femoral cut and proximal tibial cut are each made, quick pins 150 and 152, also referred to herein as securing members 150 and 152 (illustrated best in FIG. 15), or other securing devices may be placed in the resected surface of the distal femur to secure a sizing guide 60 (illustrated best in FIGS. 13 and 14) to the distal femur. The sizing guide 60 may be configured for sizing the distal femur, such that an appropriately sized femoral component may be selected by the surgeon. The sizing guide 60 may be located on the substantially flat, resected surface of the distal femur and may be secured to said substantially flat, resected surface by the quick pins 150 and 152. It will be appreciated that the quick pins 150 and 152 are initially implanted to secure the sizing guide 60, but will later be used as a reference to secure other components of the invention to the bone. For example, the sizing guide 60 and subsequent placement of the quick pins 150 and 152 determine the initial position of the A/P cutting guide device 10 on the distal femur, as the A/P cutting guide device 10 will be secured to said quick pins 150 and 152. After securing the A/P sizing guide 60 to the distal femur, a measurement may be taken utilizing the A/P sizing guide 60, which measurement may correspond to an appropriately sized femoral component, and may further correspond to the A/P cutting guide device 10.

After the quick pins 150 and 152 are placed in the bone, and measurements from the sizing guide 60 taken, the sizing guide 60 may be slid off and removed from the quick pins 150 and 152. Thereafter, the A/P cutting guide device 10 may be slid onto the quick pins 150 and 152. As will be explained herein in more detail below, the A/P cutting guide device 10 may move relative to the quick pins 150 and 152, which may be fixed to the distal femur.

Figure 2:
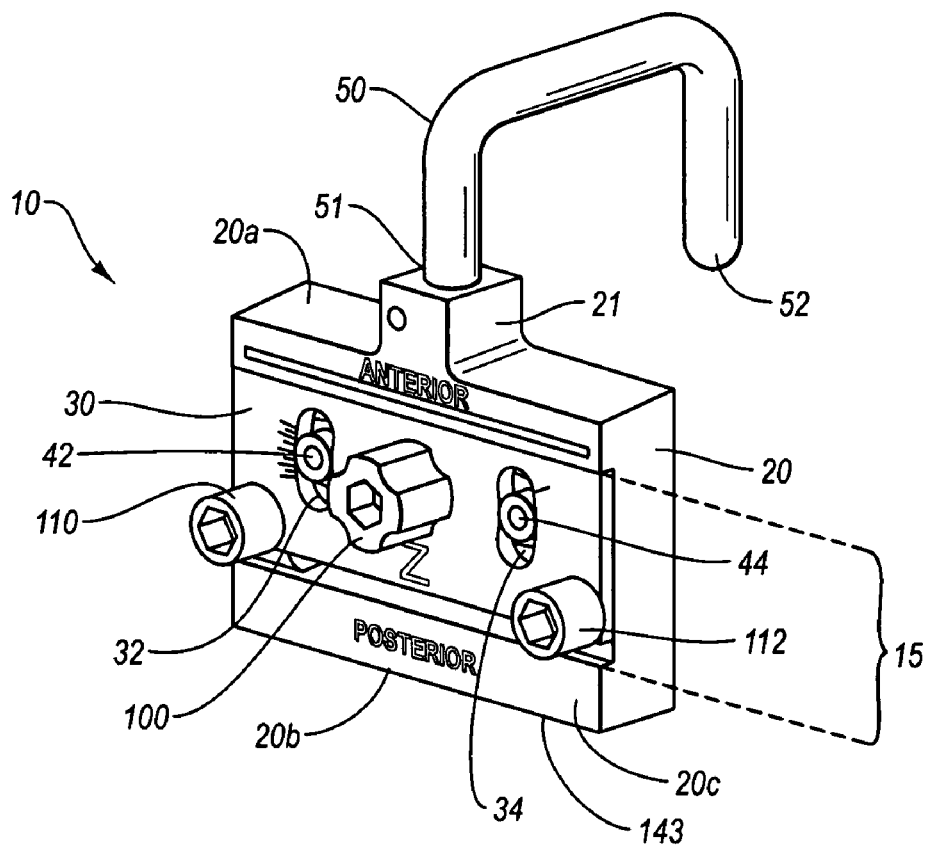
FIG. 2 is a perspective view of the A/P cutting guide device of FIG. 1, assembled in accordance with the principles of the present invention.
Figure 3:
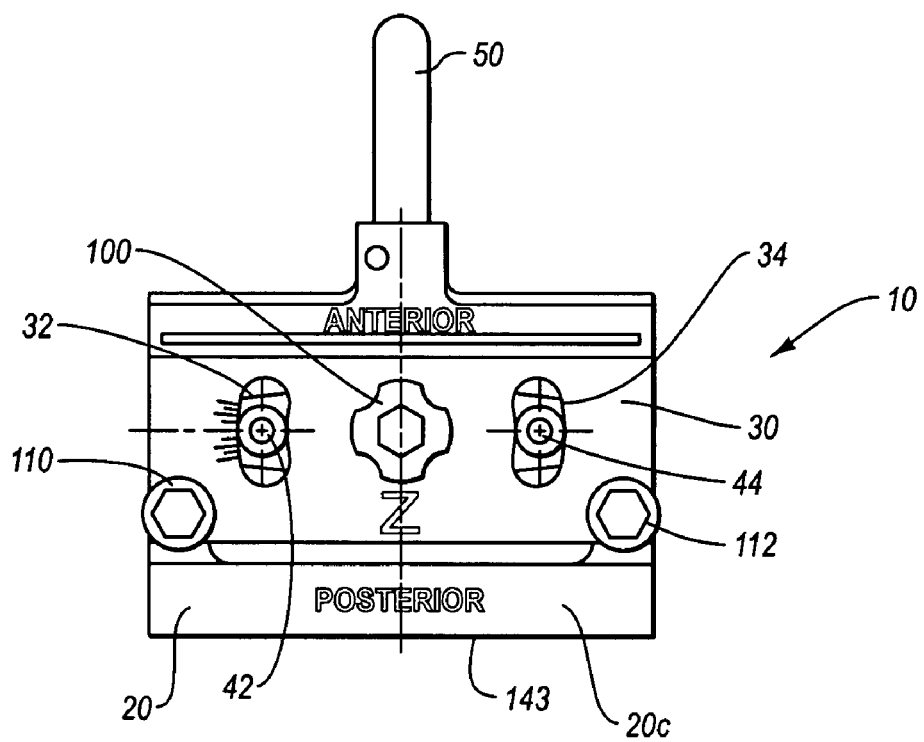
FIG. 3 is a front view of the A/P cutting guide device of FIG. 1, made and assembled in accordance with the principles of the present invention.

As illustrated in FIGS. 1-3, the cut guide member 20, also referred to herein as a cutting block 20, a cutting block member 20, and sometimes referred to herein in conjunction with its features as a means for translating the device 10, may comprise a top surface 20a, a bottom surface 20b, a face 20c, a connecting portion 21, and a recessed area 22. It will be appreciated that the recessed area 22 may be defined by sidewalls 23, an anterior border 28 and a posterior border 29, and a recessed surface 22a. The connecting portion 21 may extend upwardly from the top surface 20a of the cut guide member 20, as illustrated in FIG. 1. Connecting portion 21 may have an opening 27 configured to receive and secure the boom 50 to the cut guide member 20.

The boom 50 may comprise a first end 51 and a second end 52, the first end 51 of said boom 50 being dimensioned to fit within the opening 27 of the connecting portion 21 of the cut guide member 20, and may be configured as a reference to aid the surgeon in making an anterior cut in the distal femur. The boom 50 may further act to aid the surgeon in the avoidance of notching the femur. As used herein, "notching" refers to cutting too much of the bone, in other words over resecting a portion of the bone, such that a notch or depression is created in the bone. Notching the femur tends to create edges that cause stress risers, which have potential to cause fractures in the bone. Therefore, the boom 50 helps to reduce the occurrence of stress risers, due to notching the anterior portion of the distal femur, by acting as a reference point for the surgeon such that over resection may be avoided when making the anterior cut in the distal femur.

As illustrated in FIG. 1, the opening 27 of the connecting portion 21 may be substantially circular, but it will be appreciated that the opening 27 may be any shape to enable one end 51 of the boom 50 to fit attachably within the opening 27. It will likewise be appreciated that the boom 50 may be modified to be of any suitable shape having a cross-section that includes a substantially circular shape, as illustrated, or a substantially square shape, a substantially polygonal shape, or any other suitable shape that may be designed for use as the boom 50.

The recessed surface 22a of the recessed area 22 of the cut guide member 20 may comprise a plurality of holes, represented by items 24 and 26, that are each defined by a sidewall. As illustrated best in FIG. 3B, the holes 24 and 26 may be substantially elongated and straight, continuing in the same direction without curving, or the holes 24 and 26 may curve slightly such that a substantially kidney bean shape may be achieved, or the holes 24 and 26 may curve in a substantially arcuate manner. Of course, it will be appreciated that other substantially elongated shapes for the holes 24 and 26 may also be used without departing from the scope of the present invention., Recessed area 22, as illustrated in FIGS. 1 and 2, may be shaped in a substantially rectangular manner. However, it will be appreciated that the shape of the recessed area 22 may be modified such that any suitable shape may be utilized, including a substantially square shape, any suitable substantially polygonal shape, any suitable substantially oval shape, or any suitable substantially elongated shape. Because of the relationship that exists between the cut guide member 20 and the recessed area 22, it will be appreciated that as the shape or size of the cut guide member 20 is modified, the shape or size of the recessed area 22 may also be modified accordingly, although such modification is not necessarily required. Recessed area 22 may be configured and dimensioned to receive the support member 40 and a portion of the positioning member 30 therein. Therefore, it is to be understood that as the support member 40 and the positioning member 30 are modified, the shape of the recessed area 22 may also be modified in order to maintain the function of the recessed area 22.

The sidewalls 23 of the recessed area 22 may each comprise a wall surface, represented by items 23a and 23b, and the wall surfaces 23a and 23b may be raised with respect to the recessed surface 22a, and may be recessed with respect to the face 20c of the cut guide member 20. The wall surfaces 23a and 23b may be located medially and laterally on each side of the recessed surface 22a on the cut guide member 20. The anterior border 28, the posterior border 29, and the wall surfaces 23a and 23b define a translation area, illustrated best in FIG. 2 by bracket 15, that may be configured to receive at least a portion of the positioning member 30 therein. It will be appreciated that the cut guide member 20 may be moved in a translational manner, as will be discussed below in more detail, only as far as the translation area 15 will allow. In other words, it is possible that as the cut guide member 20 moves in the translational manner, at least a portion of the positioning member 30 may ultimately contact the anterior border 28 or the posterior border 29 of the translation area 15, limiting how far anteriorly or posteriorly the cut guide member 20 may be moved within the translation area 15. However, it will be appreciated that the positioning member 30 is not required to contact the anterior border 28 or the posterior border 29, but those borders serve to limit how far anteriorly or posteriorly the cut guide member 20 may move before the positioning member 30 contacts one of the above-referenced borders during translation.

It will be appreciated that the walls 23 may join the anterior border 28 or the posterior border 29 at a junction forming a corner 23c. It will further be appreciated that the corners 23c of the recessed area 22 may be substantially round. It should be noted that rounded corners 23c may be present at each of the junctions where the walls 23 meet the anterior or posterior borders 28 and 29, but the invention may still operate and function using corners 23c that are not rounded. For example, corners 23c that substantially form right angles at the junction of the walls 23 may be used as long as the function of the corners 23c is maintained. The function, at least in part, of said corners 23c is to permit protruding walls 31 and 33 of the positioning member 30 to rotate within the recess 22 and move about the walls 23 and the corners 23c, as illustrated best in FIG. 3C.

Figure 12:
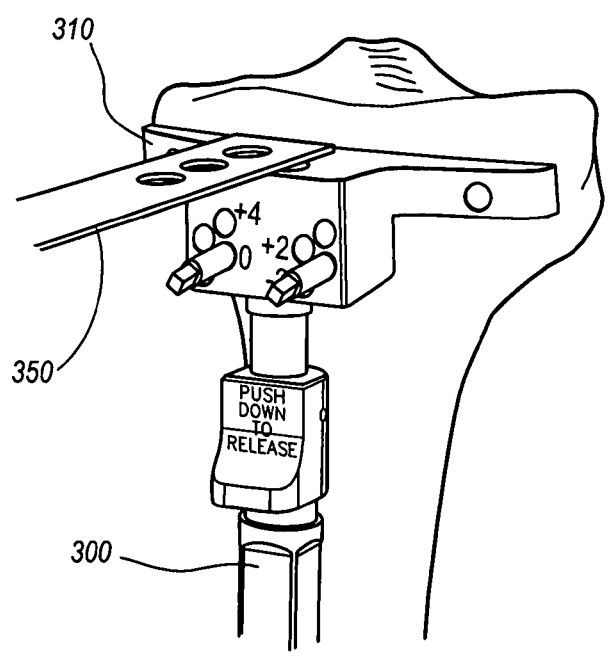
FIG. 12 is a perspective view of the proximal tibia illustrating an oscillating saw resecting the proximal tibia.

As illustrated in FIGS. 3A-3C, the cut guide member 20 may further comprise an anterior portion, represented by the bracket numbered as item 25 in FIG. 3A, and a posterior portion, represented by the bracket numbered as item 25a in FIG. 3A. The anterior portion 25 may comprise an anterior cutting guide 140 configured as a template for a cutting instrument 350, such as an oscillating saw (as illustrated in FIG. 12), to enter therein and make an anterior cut in the distal femur. The anterior cutting guide 140, as illustrated, may be essentially a slit formed within the cut guide member 20 so as to permit the cutting instrument 350 to enter therein. The anterior cutting guide 140 may slope downwardly from back 144 to front 145, and in a proximal to distal direction, of the cut guide member 20, as illustrated in FIG. 3A, such that the resulting anterior cut may be similarly sloped. It will be appreciated that the slope of the anterior cutting guide 140 may be as illustrated, or it may modified by one of skill in the art to include a greater or lesser slope angle depending upon the desired outcome of the resulting anterior cut to be made in the bone. As illustrated, the anterior cutting guide 140 slopes such that the resulting anterior cut lines-up approximately with the second end 52 of the boom 50, which may act as a reference for the surgeon.

Figure 5:
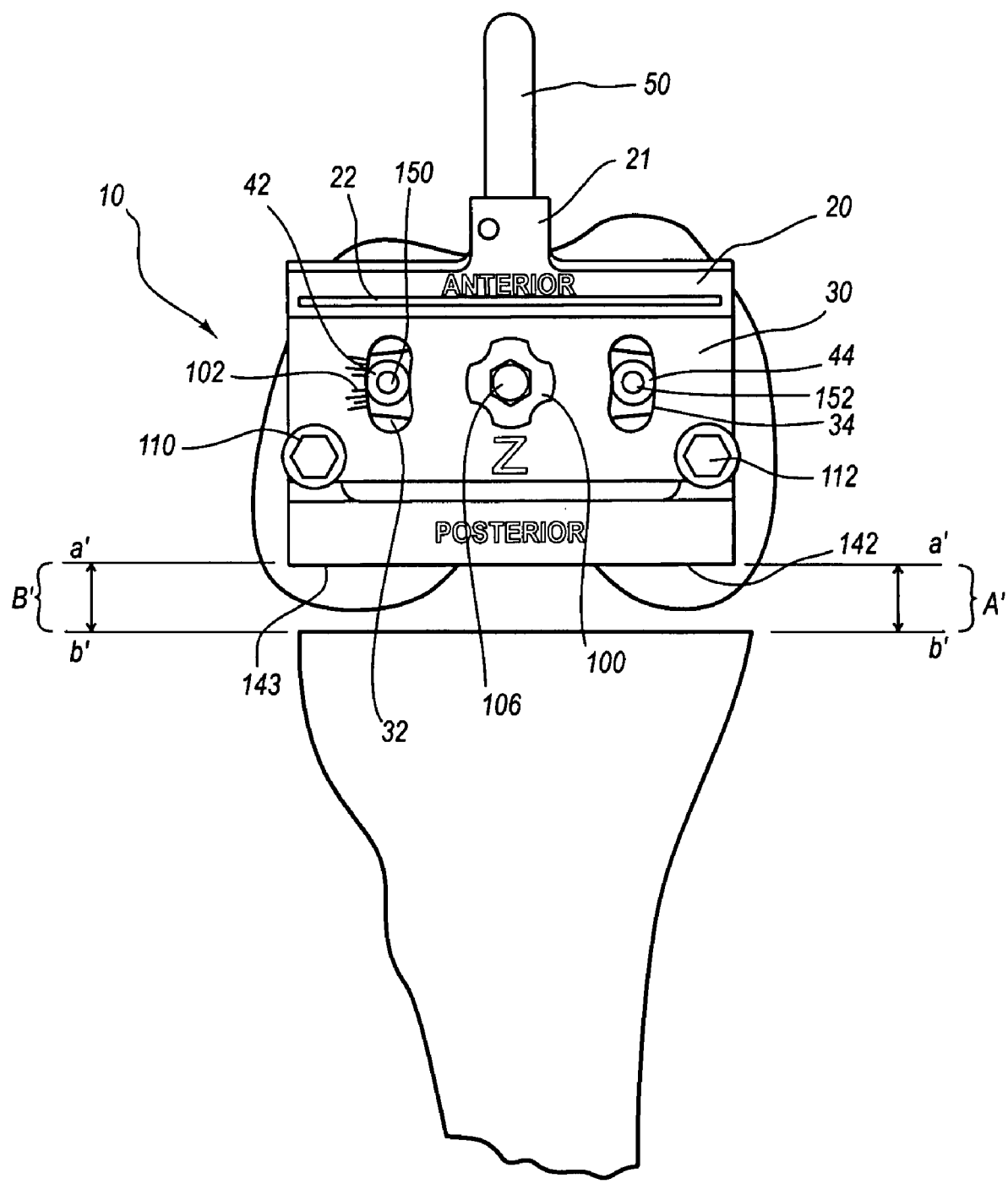
FIG. 5 is a front view of the A/P cutting guide device located on the distal end of the flexed femur, similar to FIG. 4, with the A/P cutting guide device having been rotated into alignment, in accordance with the principles of the present invention.

The posterior portion 25a of the cut guide member 20 may comprise a posterior cutting guide 142 configured as a template for making a posterior cut in the distal femur using the cutting instrument 350, such as the oscillating saw mentioned above. The posterior cutting guide 142, as illustrated, may be a bottom edge 143 of the cut guide member 20. However, it will be appreciated that the posterior cutting guide 142 may be some other surface besides the bottom edge 143 of the cut guide member 20 as long as the surface can be rotated and translated, and the surface acts as a cutting guide permitting the surgeon to make the posterior cut in the distal femur. The posterior cutting guide 142 may comprise a substantially flat surface that may enable the surgeon to place the cutting instrument 350 in contact with the substantially flat surface of the posterior cutting guide 142, and to make a cut that is substantially straight and flat. The substantially straight, flat posterior cut is a cut that may advantageously be formed substantially parallel to the proximal tibial cut creating the flexion gap 18. FIG. 5 illustrates the A/P cutting guide device 10 in proper position and alignment on the distal femur, with the patient's leg in flexion, prior to the surgeon committing to the posterior cut, such that the posterior cut if made with the A/P cutting guide device 10 in this position will result in the flexion gap 18 being substantially rectangular in shape, such that an upper side 18a of said gap 18 is substantially parallel to a lower side 18b of said gap 18 (as shown most clearly in FIG. 17). Stated in another way, the distance represented by bracket A' may be substantially equal to the distance represented by bracket B' indicating that the lines a'-a' and b'-b' are substantially parallel.

It should be noted that the posterior cutting guide 142 may be located on the bottom edge 143 of the cut guide member 20 as described above, but it should be noted that a posterior cutting guide 142 located in another location within the cut guide member 20 and having the same or a similar function as the posterior cutting guide 142 may also be used by the present invention as long as the rotational and translational capabilities of the device 10 are not interfered with.

As mentioned above, the cut guide member 20 may be configured to slide onto the quick pins 150 and 152 by utilizing holes 24 and 26, and may be secured to the quick pins 150 and 152 by utilizing both the support member 40, and the positioning member 30, as explained in more detail below. Support member 40 may comprise a plurality of through holes 46 and 48 for receiving the quick pins 150 and 152 therein in a tight matching fit, thus securing and fixing the support member 40 to the quick pins 150 and 152. It should be noted that the shape of through holes 46 and 48 may be configured to match the shape of the quick pins 150 and 152 or other securing device. Once attached to said quick pins 150 and 152, the support member 40 may be in a position of stability and may be fixed to the distal femur. Thus, the support member 40 may act as an anchor to secure the entire A/P cutting guide device 10 to the distal femur.

Support member 40, sometimes referred to herein as a first member, may further comprise a plurality of protrusions 42 and 44 that protrude from both a first side 43 and a second side 45 of the support member 40 as illustrated in FIG. 1, and may surround through holes 46 and 48 such that when the quick pins 150 and 152 are inserted into the through holes 46 and 48, the protrusions 42 and 44 may also surround the quick pins 150 and 152. It will be appreciated that while the present invention illustrates the protrusions 42 and 44 surrounding the through holes 46 and 48 such is not required. Protrusions 42 and 44 may be provided on the medial and lateral sides of a central through hole 41 for interacting with a plurality of through holes 32 and 34 of the positioning member 30, and may further interact with the holes 24 and 26 of the cut guide member 20. It should be noted that the interaction of the protrusions 42 and 44 with holes 32, 34, 24 and 26 may permit the positioning member 30 and the cut guide member 20 to move about the protrusions 42 and 44, and hence the quick pins 150 and 152, as the quick pins 150 and 152 extend through the protrusions 42 and 44.

The support member 40 may comprise an outer wall surface 47, a first end 49a, and a second end 49b. The support member 40 may comprise a cross-sectional shape that may be substantially shaped as a diamond such that the outer wall surface 47 may taper from middle reference areas 49 and 49c in the medial and lateral direction toward the first end 49a and the second end 49b, as illustrated in FIG. 1. The first end 49a and the second end 49b may be polygonally shaped such that a substantially rounded configuration may be achieved as illustrated in FIG. 1, or a truly rounded configuration may also be used without departing from the scope of the present invention. The tapering of the outer wall surface 47 may result in a height of the support member 40, as measured between the top reference area 49 and the bottom reference area 49c, that may be greater than the height of the support member 40 at either of its ends 49a and 49b.

It will be appreciated that as used herein the term "support member" may refer to: (a) a first body having at least one point, or a defined area, that acts as a hinge, or a point or area of support, about which a second body may be caused to rotate, revolve or turn; or (b) a first body having a surface about which a second body may move, with respect to the first body, in which every point of the second body moves parallel to and the same distance as every other point of said second body. It should be noted that the support member 40 may be shaped as illustrated in FIG. 1, or the shape may be modified to include a substantially oval shape, a substantially elongated shape, or any other suitable shape for utilization as a support about which other components of the invention may move. Thus, the support member 40 may be fixed to the quick pins 150 and 152 providing a stationary piece about which the positioning member 30 and cut guide member 20 may move, relative to the quick pins 150 and 152 and the distal femur.

The positioning member 30, sometimes referred to herein as a second member, and sometimes referred to in conjunction with its features as a means for attaching the cut guide member 20 to the support member 40, illustrated in FIGS. 1-3, may generally comprise a first end 30a, a second end 30b, a plurality of through holes 32 and 34, a plurality of translational through holes 36 and 38, and a central hole 39. It will be appreciated that the placement of the holes 32, 34, 36, 38, and 39 on the positioning member 30 may be as illustrated in the FIGS., or the positioning member 30 may be modified to include holes 32, 34, 36, 38, and 39 placed in different locations on said positioning member 30 without departing from the scope of the present invention. It will be appreciated that at least one of the plurality of through holes 32 and 34 may be located at or near the first end 30a and at the second end 30b of the positioning member 30. It will be appreciated that the plurality of through holes 32 and 34 may be substantially kidney bean shaped, or may be shaped in a substantially arcuate manner (illustrated best in FIG. 3), while the translational through holes 36 and 38 (illustrated best in FIG. 1) may be substantially elongated and permit lateral knobs 110 and 112 to pass therethrough, and the central hole may be configured for allowing the passage of a central knob 100 therethrough (illustrated best in FIG. 1). It will be appreciated that the shape of the through holes 32, 34, 36, and 38, and the shape of the central hole 39 may each be modified to be a substantially elongated shape, a substantially circular shape, a substantially square or rectangular shape, a substantially polygonal shape, or any other suitable shape known in the art, without departing from the scope of the present invention. It will further be appreciated that the through holes 32, 34, 36, and 38, and the central hole 39 may each be similarly shaped to one another, or they may each have their own unique shape without departing from the scope of the present invention.

Positioning member 30 may further comprise a first side 72, a second side 74, a top surface 76, a bottom surface 78, and a series of markings 102 located on the first side 72 and near at least one of the through holes 32 and 34. The series of markings 102 may correspond to a predetermined angle of rotation of the positioning member 30. The positioning member 30 may also comprise a plurality of protruding walls 31 and 33 protruding from the second side 74 of the positioning member 30. It will be appreciated that the protruding walls 31 and 33 may also extend outwardly from the second side 74 of the positioning member 30 in a substantially orthogonal manner.

It will be appreciated that protruding walls 31 and 33 may correspond in shape to the walls 23, including the corners 23c, of the cut guide member 20 such that the outer portions of the Protruding walls 31 and 33 may fit into and match the walls 23 of the cut guide member 20. The outer portion of the protruding walls 31 and 33 may be shaped substantially in a convex manner, and the inner portion of the protruding walls 31 and 33 may be substantially shaped in a concave manner in order to allow the positioning member 30 to rotate about the support member 40. Thus, the protruding walls 31 and 33 may be shaped in a substantially arcuate manner as described above.

It will be appreciated that the concavity of the inner portions of the protruding walls 31 and 33 may be such that the ends 49a and 49b of the support member 40 may articulate with the concave inner portions of the protruding walls 31 and 33 as the positioning member 30 rotates about said support member 40. It will further be appreciated that as the shape of the walls 23 of the cut guide member 20 changes, the protruding walls 31 and 33 may change accordingly such that the functions stated above may be accomplished.

Central knob 100, also referred to herein as an attachment member 100, and collectively referred to herein with its associated parts and features as a means for rotating, may comprise a knob portion 104 having an opening 106 formed therein, and a pin portion 108 configured and dimensioned for being inserted through the central hole 39 of the positioning member 30 and into the central hole 41 of the support member 40. It will be appreciated that pin portion 108 may comprise threads for threadedly engaging the central holes 41 of the support member 40, which may also be threaded. However, it will be appreciated that such a threaded configuration is not required, and the connection between the pin portion 108 and the central hole 41 may be modified to include other fastening mechanisms known in the art to secure a pin portion, such as 108, to a hole, such as 41. For example, pin portion 108 may ultimately be secured to the support member 40 by way of a fastener 109, whether or not the pin portion 108 and the central hole 41 are threaded, which fastener 109 may be a nut for example, or said fastener 109 could be any other fastening device currently known in the art, or which may become known in the future, for securing the pin portion 108 to the support member 40.

Figure 4:
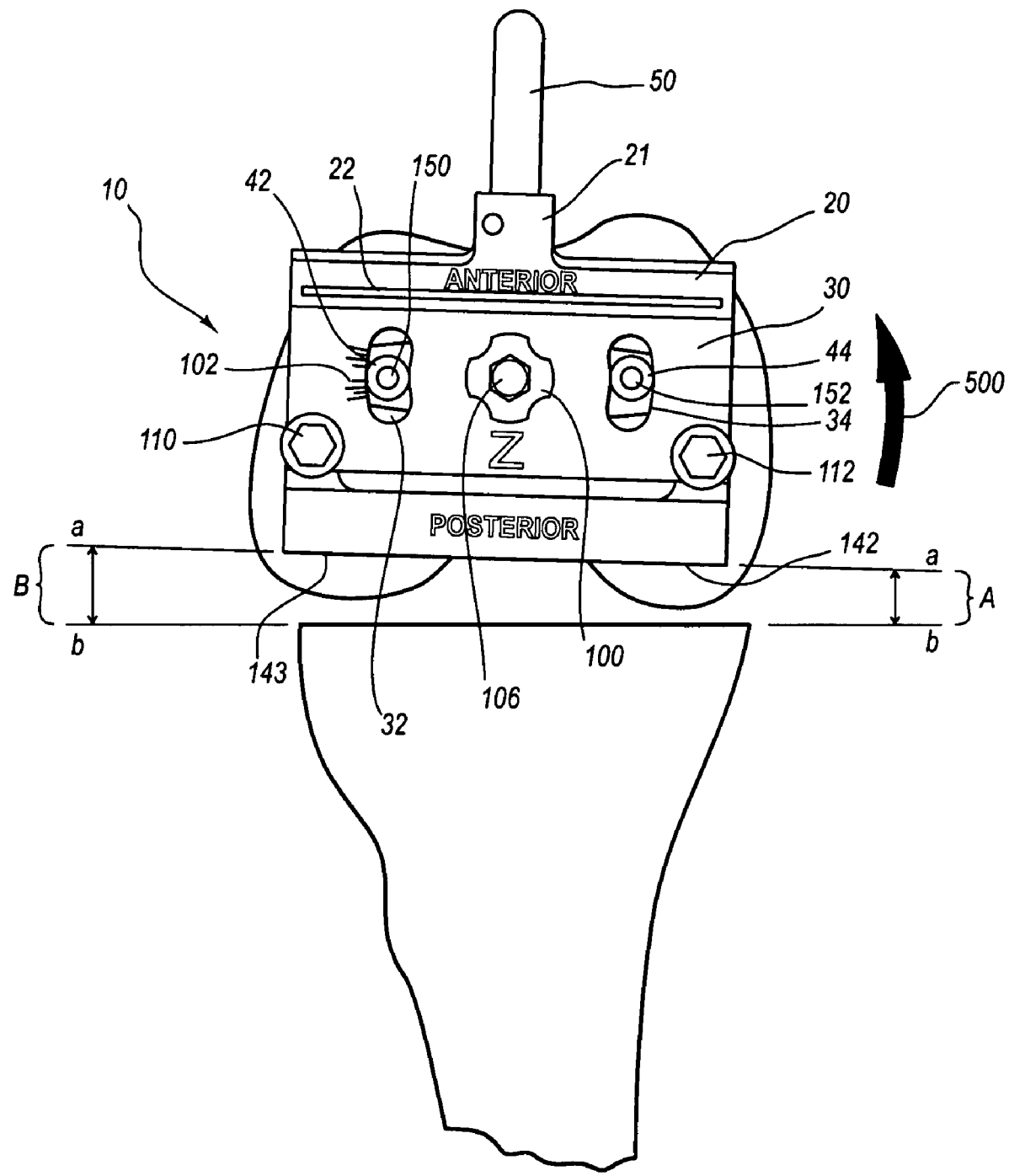
FIG. 4 is a front view of the A/P cutting guide device located on a distal end of a femur in a flexed knee joint, with the knee joint in flexion, and illustrates the A/P cutting guide device in mal-alignment with a resected portion of a proximal tibia.

Opening 106 of the knob 100 may be configured and dimensioned for receiving an instrument therein to provide the mechanism to secure the knob 100 to the support member 40. It will be appreciated that opening 106 may be substantially polygonal in shape, substantially hexagonal for example, or may be any suitable shape for receiving said instrument therein and otherwise accomplishing the stated function. It will be further appreciated that the knob portion 104 may have a cross-sectional shape that may be substantially star shaped as illustrated in FIGS. 1-3, or it may be substantially circular in shape as illustrated in FIGS. 4 and 5, or it may be substantially oblong, substantially square, substantially polygonal, or any other suitable shape for tightening and loosening the pin portion 108. It will be further appreciated that the pin portion 108 may be configured without threads as illustrated in FIG. 1, or it may comprise threads thereon for attachment to the central hole 41, or to the fastener 109, in a screwing manner. Therefore, the pin portion 108 may be, for example, threaded and function similar to a bolt and nut, or it may be unthreaded having other means for securing the pin portion 108 to the fastener 109.

Similar to the knob 100, lateral knobs 110 and 112, also referred to herein as attachment members 110 and 112, may each comprise a knob portion 118 and 120 having an opening 114 and 116 formed therein, and a pin portion 122 and 124. Pin portions 122 and 124 may be configured and dimensioned for insertion through the translational through holes 36 and 38 of the positioning member 30, passing near, but not through, the holes 46 and 48 of the support member 40, and into the lateral through holes 130 and 132 of the cut guide member 20 such that the positioning member 30 and the cut guide member 20 may sandwich the support member 40 therebetween. It should be noted that the lateral through holes 130 and 132 may also be referred to herein as receiving holes 130 and 132 for receiving attachment members 110 and 112 therein. It will be appreciated that pin portions 122 and 124 may comprise threads for threadedly engaging the lateral through holes 130 and 132, which may be threaded. However, it will be appreciated that such a threaded configuration is not required, and may be modified to include other fastening mechanisms known in the art to secure a pin portion, such as 122 and 124, to a through hole, such as 130 and 132.

For example, pin portions 122 and 124 may be ultimately secured to the cut guide member 20 by way of fasteners 123 and 125, whether the pin portions 122 and 124 and the through holes 130 and 132 are threaded or not. Fasteners 123 and 125 may be for example a nut, or any other fastening device that may hold or secure the pin portions 122 and 124 in place, whether threads have been utilized or not, thus allowing the lateral knobs 110 and 112 to essentially secure the positioning member 30 to the cut guide member 20.

Openings 114 and 116 of the attachment members 110 and 112, respectively, may be configured and dimensioned for receiving an instrument therein to provide the mechanism to secure the attachment members 110 and 112 to the receiving holes 130 and 132 of the cut guide member 20. Openings 114 and 116 may be substantially polygonal in shape, substantially hexagonal for example, or may be any suitable shape for receiving the instrument therein and for otherwise accomplishing the stated function. It will be appreciated that the knob portions 118 and 120 may be substantially circular in shape as illustrated in FIGS. 4 and 5, or may be substantially star, substantially oblong, substantially square, substantially polygonal, or any other suitable shape for tightening and loosening the pin portions 122 and 124. It will be further appreciated that the pin portions 122 and 124 may be configured without threads as illustrated in FIG. 1, or may comprise threads thereon for attachment to the lateral through holes 130 and 132, or the fasteners 123 and 125, of the cut guide member 20 in a screwing manner.

Assembly of the cut guide member 20, the positioning member 30, and the support member 40 may be accomplished in the following manner. First, position the cut guide member 20 over the quick pins 150 and 152 by placing the quick pins 150 and 152 through the holes 24 and 26 resting the cut guide member 20 on the substantially flat, resected surface of the distal femur.

Second, the support member 40 may be positioned on the quick pins 150 and 152 by inserting the quick pins 150 and 152 through the holes 46 and 48. The protrusions 42 and 44 on the second side 45 of the support member 40 may be positioned within the holes 24 and 26 of the recessed surface 22a of the cut guide member 20, allowing the support member 40 to rest within the recessed area 22 of the cut guide member 20. At this point, the support member 40 may be fixed to the quick pins 150 and 152 due to the matching fit between the holes 46 and 48, and said quick pins 150 and 152.

Third, the positioning member 30 may be placed over the quick pins 150 and 152 permitting the quick pins 150 and 152 to protrude through the holes 32 and 34. The protruding walls 31 and 33 may be inserted into the recessed area 22 such that the protruding walls 31 and 33 may engage the walls 23, including the corners 23c, if necessary, of the cut guide member 20 such that the support member 40 may be sandwiched between the cut guide member 20 and the positioning member 30. At this stage of assembly, the protrusions 42 and 44 on the first side 43 of the support member 40 may be positioned within the holes 32 and 34.

Last, assembly of the A/P cutting guide device 10 on the quick pins 150 and 152 may be completed by tightening the knob 100, by inserting the pin portion 108 through the hole 39 of the positioning member 30 and into the hole 41 of the support member 40, and securing the device 10 via the pin portion 108 and the fastener 109. The knob 100 may be thus firmly seated within the fixed support member 40, maintaining the A/P cutting guide device 10 from rotating while said knob 100 is securely fastened to the support member 40. The pin portions 122 and 124 of the knobs 110 and 112 may be inserted into the translational through holes 36 and 38 and into the lateral through holes 130 and 132 of the cut guide member 20, thus securing the cut guide member 20 to the positioning member 30. It will be appreciated that positioning member 30 may have been previously fixed to the support member 40 by the knob 100. The attachment of the knobs 110 and 112 to the through holes 130 and 132 of the cut guide member 20 may secure the cut guide member 20 to the positioning member 30, and may keep the cut guide member 20 from moving in a translational manner. Therefore, the entire A/P cutting guide device 10 may be secured to the quick pins 150 and 152.

It will be appreciated that the above described assembly steps are not intended to be the only manner in which the A/P cutting guide device 10 may be assembled. The above is merely one example of how the A/P cutting guide device 10 may be assembled and is not exhaustive of the many different combinations that may be used to assemble the device 10 on the quick pins 150 and 152. For example, the positioning member 30 may be secured to the support member 40 prior to securing the support member 40 to the quick pins 150 and 152. Other combinations may be used to assemble the A/P cutting guide device 10 on the bone without departing from the scope of the invention.

It should be noted that the support member 40 may be fixed to the distal femur by way of quick pins 150 and 152. Support member 40, being a fixed member, essentially may not move in a rotational or translational manner relative to the distal femur while connected to the quick pins 150 and 152. However, the support member 40 may be removed from the quick pins 150 and 152, and may not be permanently fixed to the quick pins 150 and 152, but rather may be temporarily fixed.

It should be noted that the positioning member 30 and the cut guide member 20 may rotate together about the support member 40, after the A/P cutting guide device 10 has been secured to the quick pins 150 and 152 which have been secured to the bone, to thereby adjust the device 10 in a rotational manner. Specifically, the rotation of the positioning member 30 and the cut guide member 20 may be accomplished by selectively loosening the knob 100 to thereby release the positioning member 30 from fixation with the support member 40, allowing the combination of the positioning member 30 and the cut guide member 20 to rotate together about a pivot. The pivot may comprise at least one of the first end 49a and the second end 49b of the fixed support member 40. It will be appreciated that the combination of the positioning member 30 and the cut guide member 20 may rotate within the limits of the through holes 32 and 34 of the positioning member 30. After the desired rotational movement has occurred, the knob 100 may be tightened returning the positioning member 30 and the cut guide member 20 to a secure position with the support member 40. Thus, the knob 100 may allow for the adjustment of the positioning member 30 and the cut guide member 20 combination in a rotational manner. It will be appreciated that the term "pivot" as used herein may refer to at least a part of an object on which another object moves, depends, or turns.

The knobs 110 and 112, on the other hand, may allow adjustment of the cut guide member 20 to occur, and specifically translational movement of the cut guide member 20 in the anterior/posterior direction. Translational movement may be accomplished by selectively loosening the knobs 110 and 112 to thereby release the cut guide member 20 from fixation with the positioning member 30 and the support member 40, and moving the cut guide member 20 anteriorly or posteriorly within the limits of the translation area 15. As noted above, the positioning member 30 may be configured and dimensioned to reside loosely within the recessed area 22 of the cut guide member 20 such that controlled translational movement of the cut guide member 20 may be permitted. In other words, the positioning member 30 and the support member 40 may remain fixed while translational movement of the cut guide member 20 occurs, such that the loose configuration of the positioning member 30 within the recessed area 22 permits the cut guide member 20 to slide anteriorly or posteriorly, because the cut guide member 20 may no longer be connected to the positioning member 30, or in other words the cut guide member 20 may be releasably attached to the positioning member 30. The cut guide member 20 may thus be able to move freely within the limits of the translation area 15 until contact is made between the top surface 76 or bottom surface 78 of the positioning member 30 and the anterior border 28 or the posterior border 29 of the translation area 15. After the desired translational movement has occurred, the knobs 110 and 112 may be tightened, securing the cut guide member 20 to the positioning member 30 and the support member 40.

To summarize, after the A/P cutting guide device 10 has been pinned to the bone using the quick pins 150 and 152 (illustrated best in FIGS. 4 and 5), the knob 100 may be selectively loosened to permit the positioning member 30 and the cut guide member 20 combination to move about the support member 40 in a limited rotational manner relative to the support member 40 fixed to the distal femur. The knobs 110 and 112, on the other hand, may be selectively loosened to permit the cut guide member 20 to slide in a translational manner in the anterior/posterior direction, independent from the positioning member 30 and the fixed support member 40, and relative to the distal femur.

It will be appreciated that the positioning member 30 may be selectively released by the surgeon from the support member 40, and the cut guide member 20 may be selectively released by the surgeon from the positioning member 30. It should therefore be noted that the cut guide member 20 and the positioning member 30 may be secured to one another such that they may move together about the first end 49a and the second end 49b of the support member 40, when said positioning member 30 is selectively released from said support member 40.

It should further be noted that the cut guide member 20 may be secured to the positioning member 30 such that when the cut guide member 20 is selectively released from said positioning member 30, the cut guide member 20 may thereby be permitted to move with respect to said support member 40 independently from said positioning member 30. Thus, it will be appreciated that the surgeon may selectively adjust the device 10, prior to committing to a cut in the bone, in both a rotational and translational manner while at least a portion of the device 10 may be anchored to the bone.

Therefore, the present invention acts as a unique A/P cutting guide device 10 for making anterior and posterior cuts in the distal femur to form the substantially rectangular extension and flexion gaps 16 and 18, and has the ability to move in said rotational manner and to slide in said translational manner, relative to the quick pins 150 and 152. It should be noted that after the device 10 has been attached to the distal femur by said quick pins 150 and 152, the device 10 may be adjusted rotationally and translationally without removing or replacing the quick pins 150 and 152. The device 10 may permit the surgeon to balance the soft tissues of the knee and to make several intermittent checks during surgery before committing to a final posterior cut in the bone, forming the flexion gap 18.

It will be appreciated that a device made in accordance with the principles of the present invention may embody more or less than the above described structural components and need not comprise all of the stated structural components. It will be further appreciated that the device may not utilize the cut guide member 20, the support member 40, or the positioning member 30 as separate components, but instead may combine one or more components into a single component, or may modify the device to combine structural features from one component and move that feature to another component without departing from the scope of the present invention. For example, the principles of the present invention may be applied to incorporate the function of the positioning member 30 into a single cut guide member 20 without departing from the scope of the present invention. It should be noted that the structural features described above may be modified by one of skill in the art to provide the same or similar functions without departing from the scope of the invention and such modifications are therefore intended to fall within the scope of the present invention.

Having described the structural components of the A/P cutting guide device 10, several illustrative examples of how the device 10 may be advantageously used will now be described. Referring now to FIGS. 4 and 5, the flexed knee is illustrated with the A/P cutting guide device 10 located on the distal end of the femur. FIG. 4 illustrates the A/P cutting guide device 10 as being completely assembled on the distal femur. As illustrated, the device 10 is mal-aligned on the distal femur such that the posterior cutting surface 142 of the A/P cutting guide device 10, and the posterior femoral cut that would result from such positioning of the device 10 represented by dashed lines a-a, is not substantially parallel with the line created by the resection of the proximal tibia, represented by dashed lines b-b. Therefore, the distance represented by bracket A may be less than (as illustrated), or greater than, the distance represented by bracket B indicating that the two lines a-a and b-b are not substantially parallel. If the posterior cut were made with the A/P cutting guide device 10 in this orientation, the flexion gap 18 would substantially be an imperfect rectangle, resulting in an unbalanced knee. This scenario is a common occurrence in TKA surgeries and correctable with prior art devices by removing the quick pins and repositioning the device in an attempt to properly balance and align the knee.

However, utilizing the A/P cutting guide device 10 of the present invention, the mal-alignment may be corrected without removing the quick pins 150 and 152. By loosening the knob 100, the positioning member 30 and the cut guide member 20 may rotate together about the support member 40, which has been fixed to the quick pins 150 and 152. Specifically, in this scenario the device 10 may be rotated in the direction of arrow 500 in FIG. 4, such that proper alignment may be achieved. Proper alignment may be checked using a spacer block 230 (see FIGS. 17 and 19) to identify where the cut will be made and whether the spacer block 230 will fit within the gap in the proper and desirable substantially rectangular alignment. It will be appreciated that the spacer block 230 may have a thickness "T1" that relates to a thickness "T2" of those portions of the prosthetic knee implant that may be configured and dimensioned to fit within the flexion and extension gaps 18 and 16. More specifically, and in reference to FIG. 19, the thickness "T1" of the spacer block 230 may relate to, and may be substantially equal to, the combined thickness "T2" of a tibial polyethylene insert 400, at least a portion of a tibial tray 405, and at least a portion of a femoral component 410 (as demonstrated in FIG. 19), which may be configured to fit within the flexion and extension gaps 18 and 16. FIG. 19 illustrates the prosthetic knee implant in an extended position, and the thickness "T2" of those portions of the prosthetic knee implant that may be inserted specifically into the extension gap 16. However, it will be appreciated that the thickness "T2" will remain substantially the same when the femoral component 410 moves into a flexed position (not illustrated in FIG. 19). Therefore, the thickness "T1" of the spacer block 230 may relate to the thickness "T2" of those portions of the prosthetic knee implant that may fit within the extension and flexion gaps 16 and 18. Therefore, a spacer block 230 that fits properly within the flexion gap 18 and extension gap 16, will result in a prosthetic knee implant that may fit properly within said gaps 18 and 16, with respect to the thickness "T2" of those portions of the prosthetic knee implant that fit within the flexion gap 18 and extension gap 16.

Once proper alignment has been determined as illustrated in FIG. 5, the knob 100 may be tightened, securing the positioning member 30 and the cut guide member 20 to the support member 40. At this stage, the posterior cutting surface 142, and the resulting posterior femoral cut represented by dashed lines a'-a', will be substantially parallel with the resected portion of the proximal tibia, represented by dashed line b'-b'. Thus, the distance represented by bracket A' may be substantially equal to the distance represented by bracket B' indicating that the lines a'-a' and b'-b' are substantially parallel. By making the posterior cut while the device 10 is in this orientation, the rectangular flexion gap 18 will be created, ultimately resulting in a properly balanced and aligned knee.

Referring now to FIGS. 6-18, the surgical technique and method of using the present invention will now be described. It will be appreciated that the invention will be described with reference to a TKA surgery, several steps of which may be familiar to one of skill in the art. Some of the previously known steps will be generally referred to herein, but may not be specifically addressed.

Generally, prior to surgery a surgeon will conduct a preoperative examination of the patient, make a diagnosis, and make other preparations that may be required to assess the patient's needs. Once these preliminary steps have been completed, the surgeon is ready to perform the TKA surgery.

Figure 6:
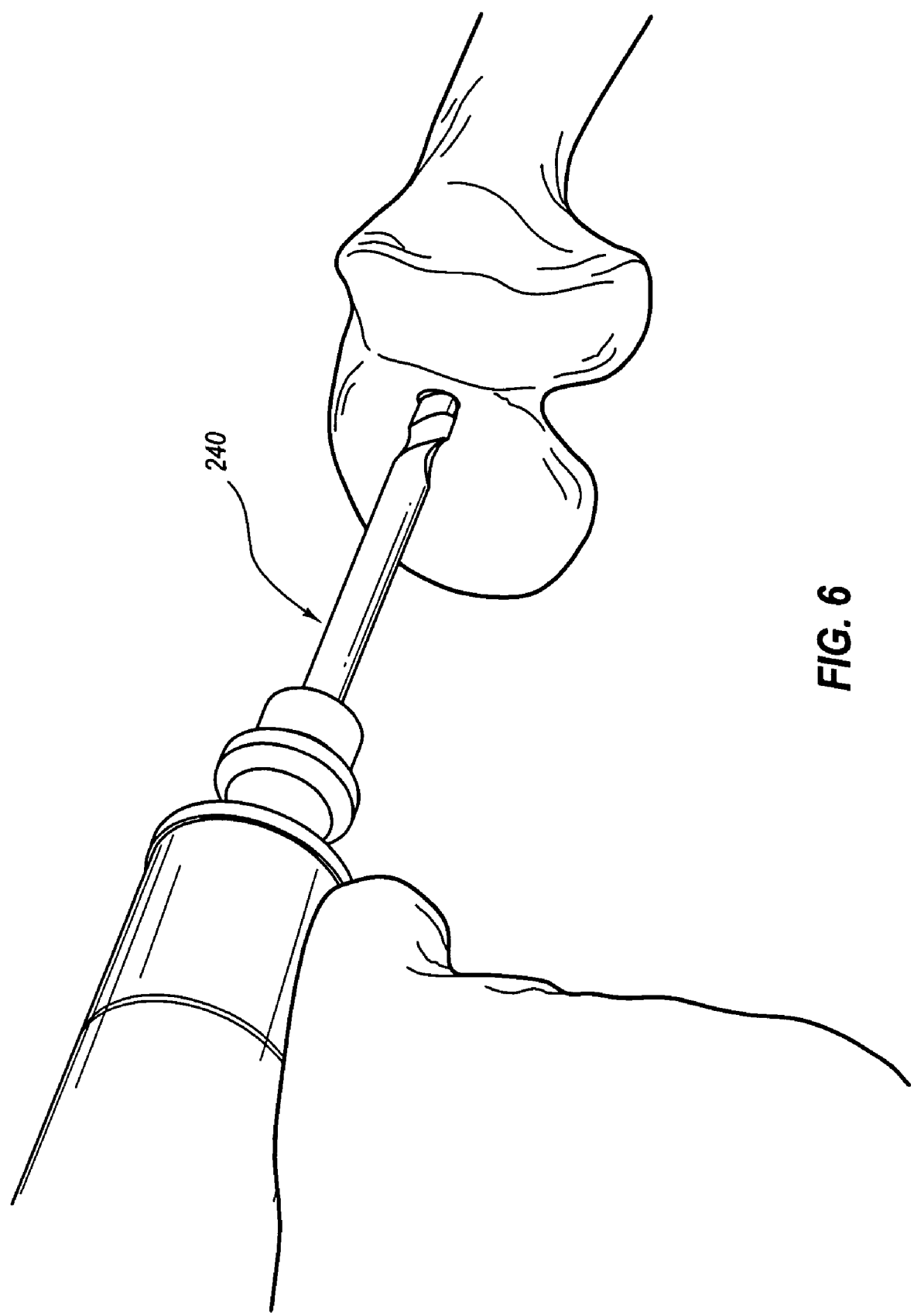
FIG. 6 is a perspective view of the distal end of the femur illustrating a surgeon beginning to drill a hole parallel to a shaft of the femur.
Figure 7:
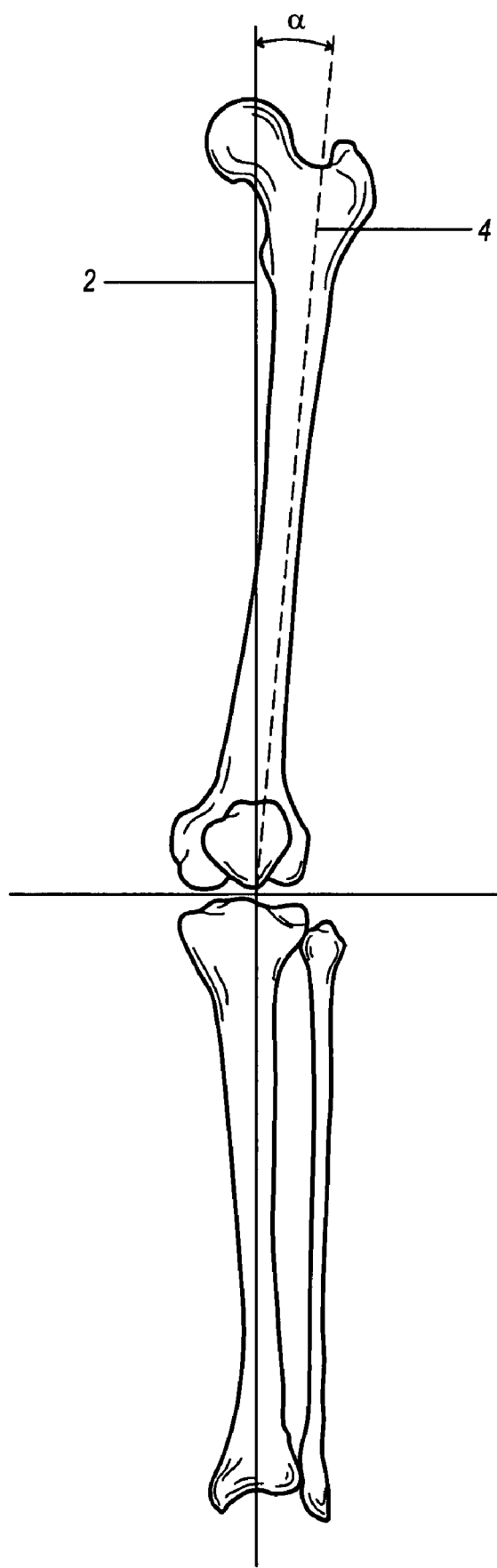
FIG. 7 is a front view of the bones that comprise a natural knee joint, illustrating a valgus angle of the knee joint, a neutral mechanical axis of the limb, and an anatomical axis of the femur.

The first step of the procedure may be to expose the surgical site, by making an anterior midline incision, after which the joint may be entered. Thereafter, the surgeon enters the medullary canal of the femur using a standard surgical drill 240 by drilling a hole just medial and superior to the center of the intercondylar notch in order to parallel the femoral shaft, as illustrated in FIG. 6. After drilling an appropriately sized hole, the surgeon inserts a T-handle 180 into the medullary canal to decompress the marrow content. At this point the surgeon may remove the T-handle 180 and slide it through an intra medullary (I/M) alignment guide 190, where the surgeon may set and lock the I/M alignment guide 190 at an appropriate valgus angle, represented in FIG. 7 as the angle α. The valgus angle α may be determined preoperatively as part of the preparation process. FIG. 7, illustrates the valgus angle α, and a neutral mechanical axis 2 of the limb. It will be appreciated that the neutral mechanical axis 2 of the limb is a line that passes from the femoral head through the center of the knee and through the center of the ankle. It will further be appreciated that the valgus angle α is the angle between the neutral mechanical axis 2 of the limb and an anatomical axis 4 of the distal femur.

Figure 8:
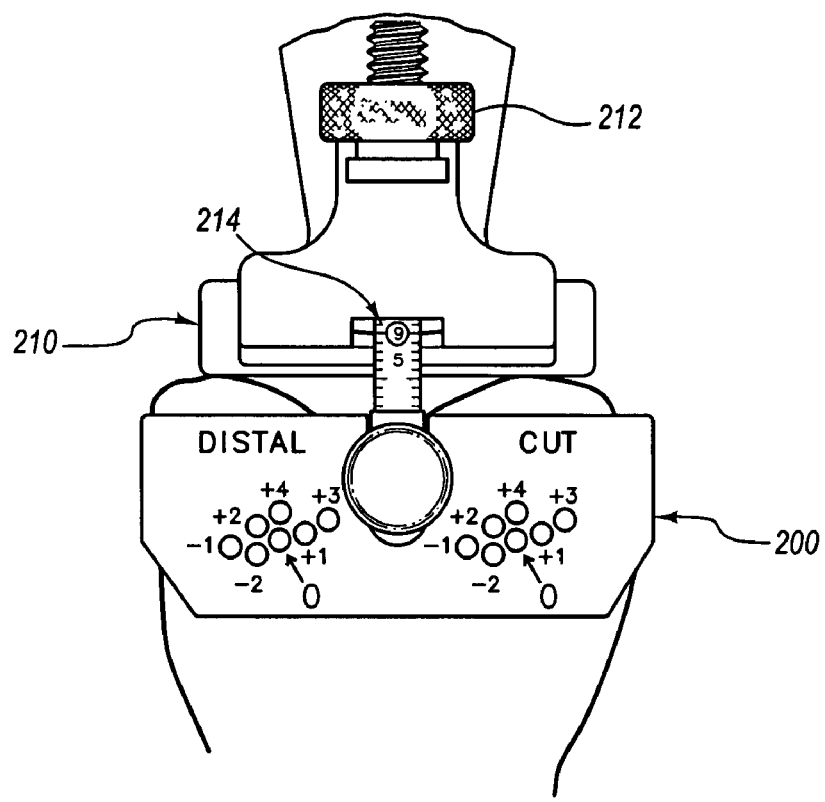
FIG. 8 is a front view of a distal cut guide located on the distal end of the femur for making an initial distal cut of the femur, in accordance with the principles of the present invention.
Figure 9:
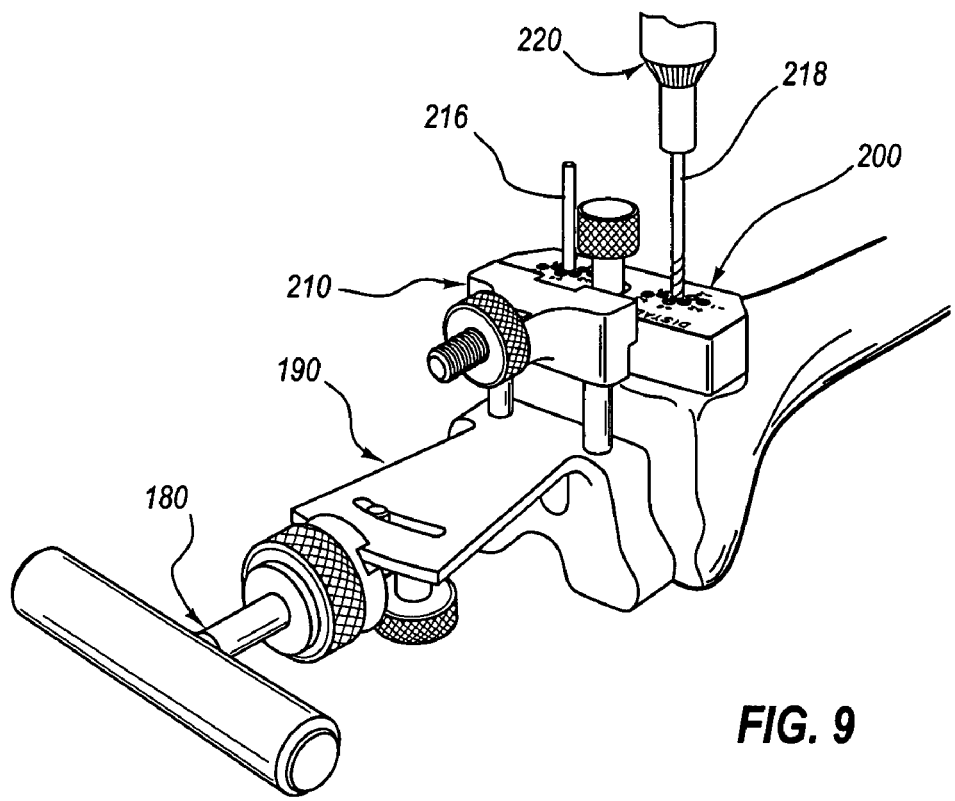
FIG. 9 is a perspective view of the cut guide of FIG. 8, illustrating the placement of a plurality of quick pins securing the cut guide to the distal femur.

More specifically and referring to FIGS. 8 and 9, after the above preparation takes place, a distal cut guide 200 may be assembled to a distal cut guide scaffolding 210, which results in an assembly. The resulting assembly may be inserted into the I/M alignment guide 190 and lowered onto the anterior cortex of the femur. The distal cut guide 200 may be adjusted proximally or distally in order to control the amount of distal femur to be resected. Adjustments may be made by rotating an adjustment knob 212, which may be located on the distal cut guide scaffolding 210, using a measurement guide 214 to view the measurement corresponding to the amount of femur to be resected. Once the appropriate amount of distal femur to be resected has been set, the distal cut guide 200 may be secured to the anterior cortex using a quick release pin driver 220 to secure quick pins 216 and 218 to the bone. After the distal cut guide 200 has been secured to the bone, the T-handle 180, I/M alignment guide 190, and the distal cut guide scaffolding 210 may be removed from the bone, leaving the distal cut guide 200 in place. Using the oscillating saw, or any other cutting instrument known in the art for resecting bone, the distal femur may be resected.

Figure 10:
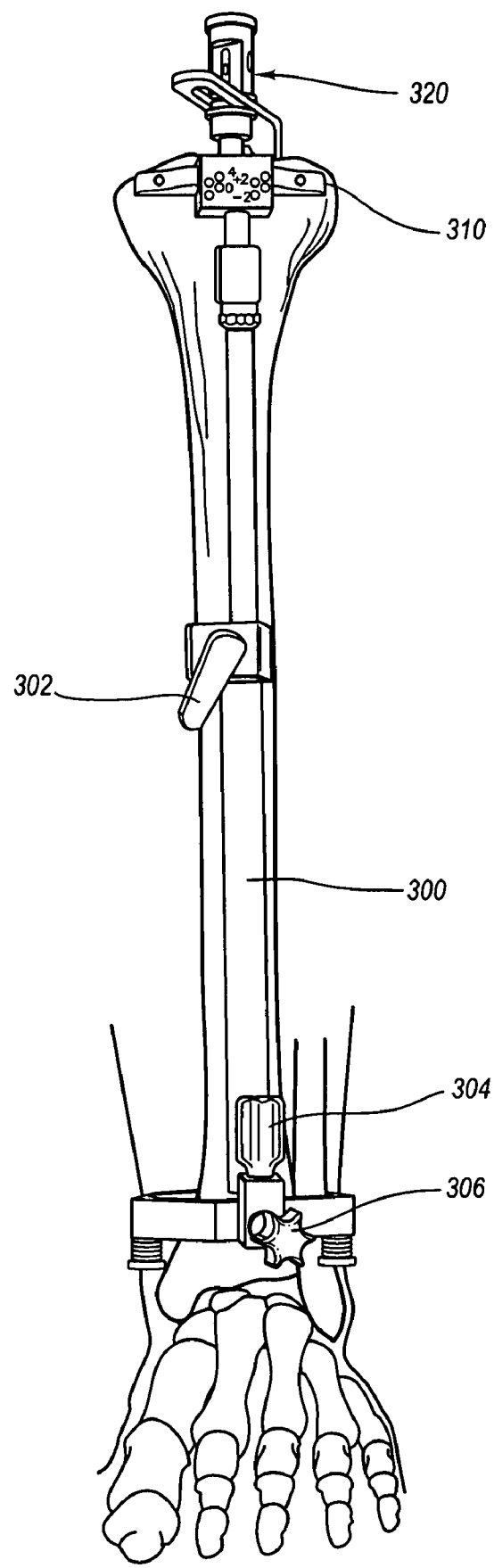
FIG. 10 is a front view of the tibia with a tibial alignment guide, a tibial cut guide and a tibial stylus located thereon.
Figure 11:
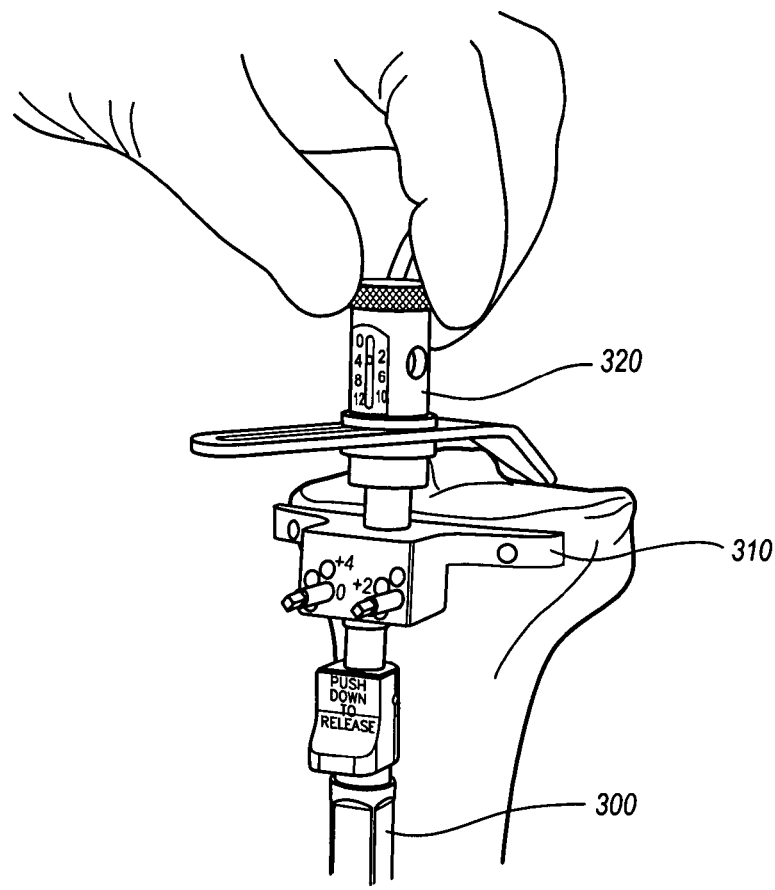
FIG. 11 is a perspective view of the proximal tibia illustrating the specifics of the tibial cut guide and tibial stylus.

The next step in the procedure includes resecting a portion of the proximal tibia, by utilizing similar instrumentation used in conjunction with the distal resection of the femur. As generally illustrated in FIGS. 10-12, the tibial instrumentation may include a tibial alignment guide 300, resection depth adjustment 302, a tibial cut guide 310, and a tibial stylus 320 to adjust the tibia to the desired depth to be resected. The tibial alignment guide 300 may further comprise a posterior slope adjustment knob 304 and a varus (medial)/valgus (lateral) adjustment knob 306 for properly aligning the tibial cut guide 310 on the tibia. Typically, the tibial resection will include about 8 mm from the prominent side or 2 mm from the deficient side of the tibia. However, it will be appreciated that more or less tibia may be resected depending upon the anatomy and deformities present in a particular patient. It will further be appreciated that a top surface of the tibial cut guide 310 may comprise a posterior slope between the range of about 0 degrees to about 7 degrees depending upon the patient's anatomy. As with the femoral distal cut guide 200, after the tibial cut guide 310 has been pinned to the bone, the stylus 320 may be removed and the tibial cut guide 310 utilized for resecting the tibial plateau.

The next step in the procedure includes checking the extension gap 16 that has been created between the distal femoral cut and the proximal tibial cut by using the appropriately sized spacer block 230. At this stage, ligament balancing may occur while the knee is in extension. To balance the ligaments, a spreader instrument (not illustrated) may be used to tense the ligaments to capacity. At this point the surgeon may surgically cut minor nicks in the ligament to stretch the ligaments. However, care should be taken to avoid over stretching of the ligaments. Stretching of the ligaments may be performed by the surgeon until the ligaments are properly balanced and the extension gap is substantially rectangular. When the knee is balanced, the surgeon moves onto the next stage of the procedure. However, if the knee is not balanced, deformities may be surgically corrected using the appropriate instrumentation until the knee is balanced. Once extension balancing has been performed, the surgeon places the knee into flexion, and moves to the next stage of the procedure.

Figure 13:
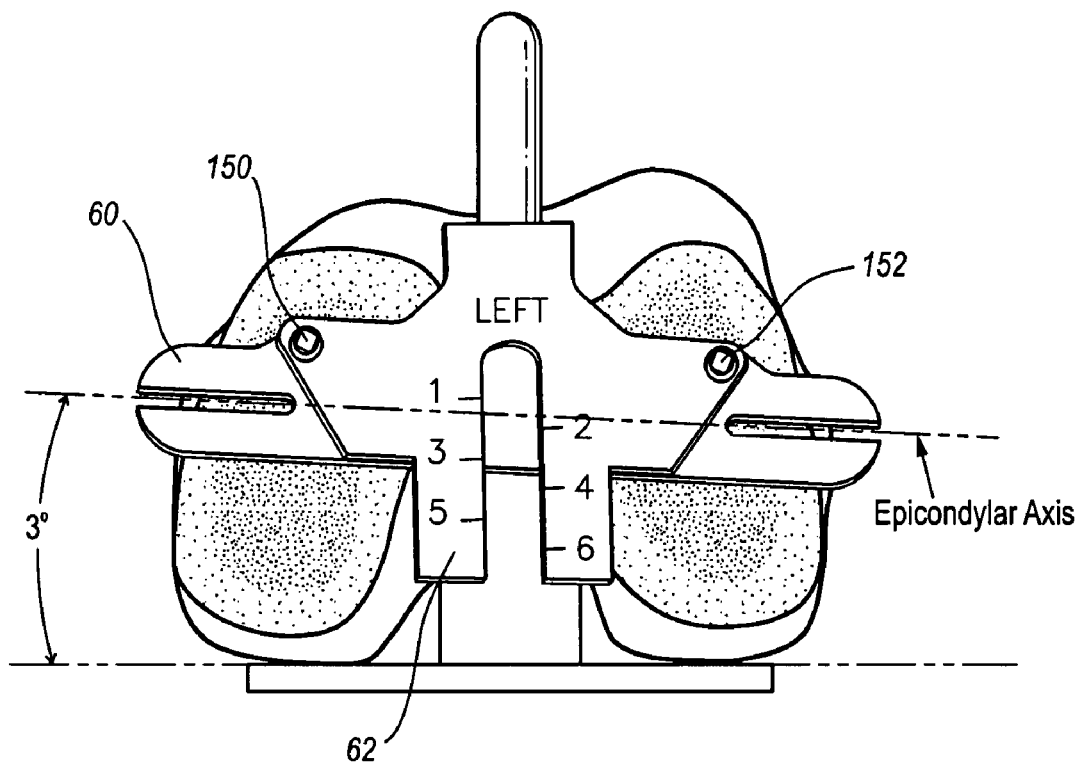
FIG. 13 is a top, front view of an A/P sizing guide located on the distal end of a typical femur after the initial distal cut has been made, wherein an epicondylar axis is illustrated.
Figure 14:
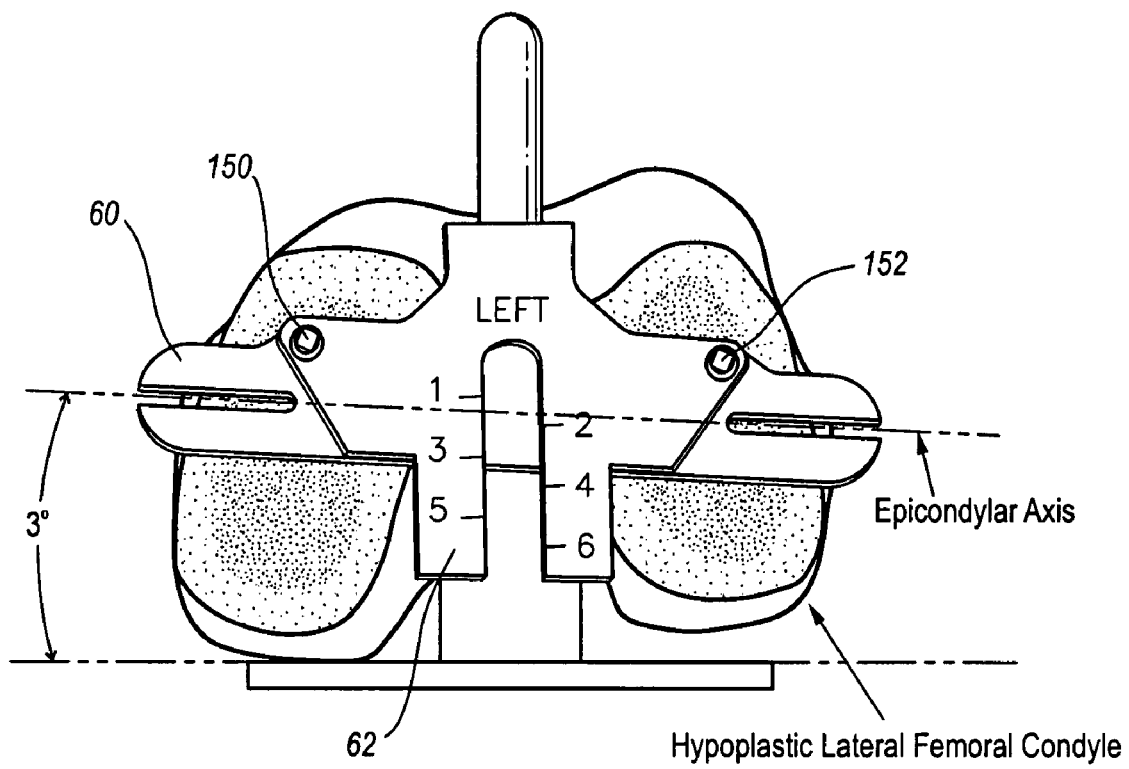
FIG. 14 is a top, front view of the A/P sizing guide similar to FIG. 13, illustrating the placement of the A/P sizing guide on an atypical femur, specifically illustrated is a hypoplastic lateral femoral condyle.

Referring now to FIGS. 13 and 14, with the knee in flexion, the femoral component may then be sized by utilizing the A/P sizing guide 60. The A/P sizing guide 60 may be configured to be placed on the resected portion of the distal femur such that the back side of the A/P sizing guide 60 may be seated flush with, and in the center of the resected portion of the distal femur. At this stage, the surgeon makes note of the femoral component size reading indicated by markings 62. The number on the A/P sizing guide 60 may correspond to a number located on the A/P cut guide member 20 indicating the initial size of the femoral component to be used, as illustrated in FIG. 16.

If the reading on the A/P sizing guide 60 indicates a marking that lies between sizes, the surgeon may begin by upsizing to the next larger component. For example, if the reading indicates a marking between size 3 and size 4, a size 4 component may be used because the components can always be downsized later. It should be noted that an increase in component size will result in less posterior femur being cut because of the space that the cut guide member 20 takes up on the distal femur. After the sizing guide 60 has been properly placed on the resected portion of the femur, quick pins 150 and 152 may be inserted through the holes in the A/P sizing guide 60 and into the bone, securing the A/P sizing guide 60 to the distal femur. It will be appreciated that the placement of the quick pins 150 and 152 may be a process that will affect the placement of subsequent instrumentation, and extra attention may therefore be required. However, it will be appreciated that the present invention does not require exact placement of the quick pins 150 and 152, due to the rotational and translational features described herein.

Figure 15:
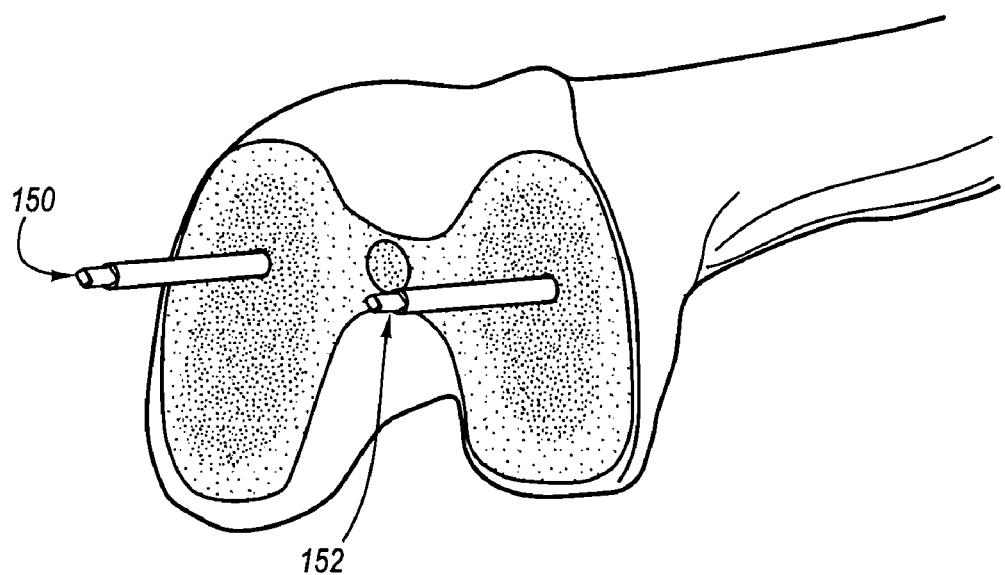
FIG. 15 is a perspective view of a plurality of quick pins that have been secured to the distal femur, to which the A/P cutting guide device will be secured, in accordance with the principles of the present invention.
Figure 16:
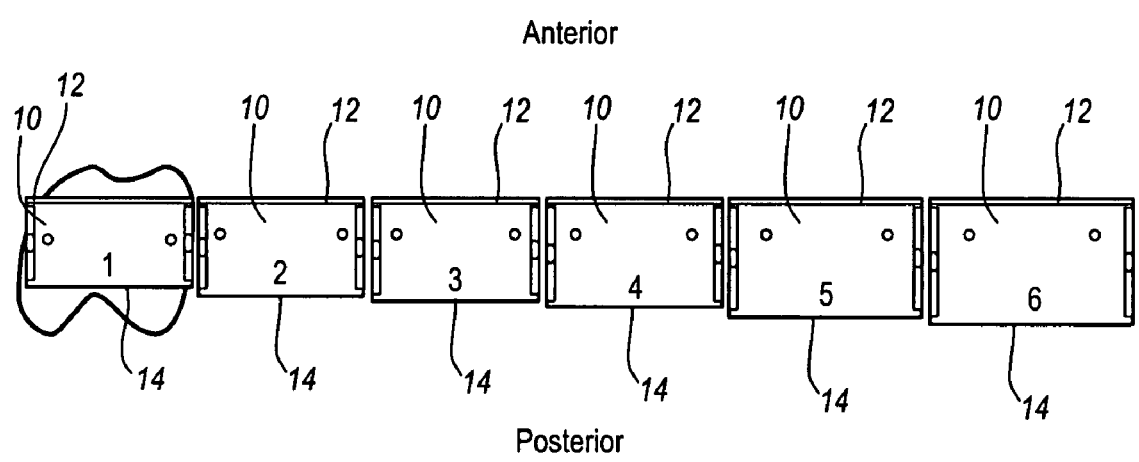
FIG. 16 is a top, front view of several different size representations of the A/P cutting guide device, illustrating the relationships of the differing sizes of the A/P cutting guide devices.

Referring to FIGS. 15 and 16, after the femoral component has been sized, the A/P sizing guide 60 may then be removed from the quick pins 150 and 152 leaving an essentially bare distal femur as illustrated in FIG. 15. FIG. 16, while not an exact replica of the A/P cutting guide device 10 of the present invention, illustrates six different representations of the various sizes that the cutting device 10 of the present invention may be made.

As illustrated, the anterior portion 12 of the device 10 may be designed such that its size does not change. In other words, the anterior portion 12 may be configured to remain in the same location on the bone and does not change size. It will be appreciated that each device 10 may differ with respect to the posterior cutting surface 14. As illustrated by the device 10 in the number 1 position of FIG. 15, the anterior portion 12 of the device 10 may maintain the same position on the distal femur, but more or less of the posterior portion of the distal femur may be resected by choosing a larger or smaller device 10. The following relationship holds true for the selection of the proper size of the device 10. The smaller the amount of distal femur to be resected, the larger the device 10. This relationship holds true because more of the distal femur may be covered by a larger device 10, and therefore, less distal femur may be exposed for resection.

The next step in the procedure includes placing the desired size of the A/P cutting guide device 10 on the femur. This may be accomplished by the process described above in relation to the description of the structural features of the device 10. The process may essentially comprise positioning the cut guide member 20 over the quick pins 150 and 152, positioning the support member 40 over the quick pins 150 and 152, placing the positioning member 30 over the quick pins 150 and 152, and securing the above components utilizing the knobs 100, 110 and 115.

At this stage, with the knee in flexion, the ligaments may once again be tensed to capacity and rotational adjustments may then be made such that the A/P cutting surface may be substantially parallel with the tibial cut, as described above in relation to FIGS. 4 and 5. Briefly stated, the rotation of the device 10 may be accomplished by loosening the knob 100, releasing the positioning member 30 and the cut guide member 20 from the support member 40, allowing rotation of the positioning member 30 and the cut guide member 20 together as a unit (illustrated best in FIG. 1).

The surgeon may then make a check of the flexion gap 18 prior to committing to the posterior femoral cut. This may be accomplished by using the spacer block 230 to visually check the orientation of the A/P cutting guide device 10 by placing the spacer block 230 on the A/P cutting guide device 10, or next to the proximal tibial cut, to determine whether the A/P cutting guide device 10 has been properly aligned.

If necessary, translational adjustments may then be made. It will be appreciated that the purpose in making the posterior cut is to create a flexion gap 18 that may be substantially equal in size to the extension gap 16, such that the ligaments will be properly balanced, which balancing has previously taken place. Before committing to the posterior femoral cut, the visual check referred to above may be used to determine whether the spacer block 230, which generally relates to the thickness of the prosthetic components configured to fit within the gap 18, will fit too tightly or too loosely in the flexion gap 18. If the flexion gap is too tight, then the A/P cutting guide device 10 may be moved anteriorly such that more distal femur may be cut during the posterior cut. Conversely, if the flexion gap 18 is too loose, then the A/P cutting guide device 10 may be moved posteriorly such that less distal femur may be cut during the posterior resection.

Such translational movement may be accomplished as stated above, and basically occurs by loosening the knobs 110 and 112 releasing the cut guide member 20 from the positioning member 30 and the support member 40. Because the cut guide member 20 has been released from the positioning member 30 and the support member 40, which has been previously fixed to the quick pins 150 and 152, the cut guide member 20 may be free to move within the confines of the translational through holes 36 and 38 as well as within the translational area 15. At this stage, before proceeding with the posterior cut, the A/P cutting guide device 10 may be positioned on the distal femur such that the flexion gap 18 will be substantially equal to the extension gap 16. Adjustments may be made as necessary to accomplish such equalization.

Figure 17:
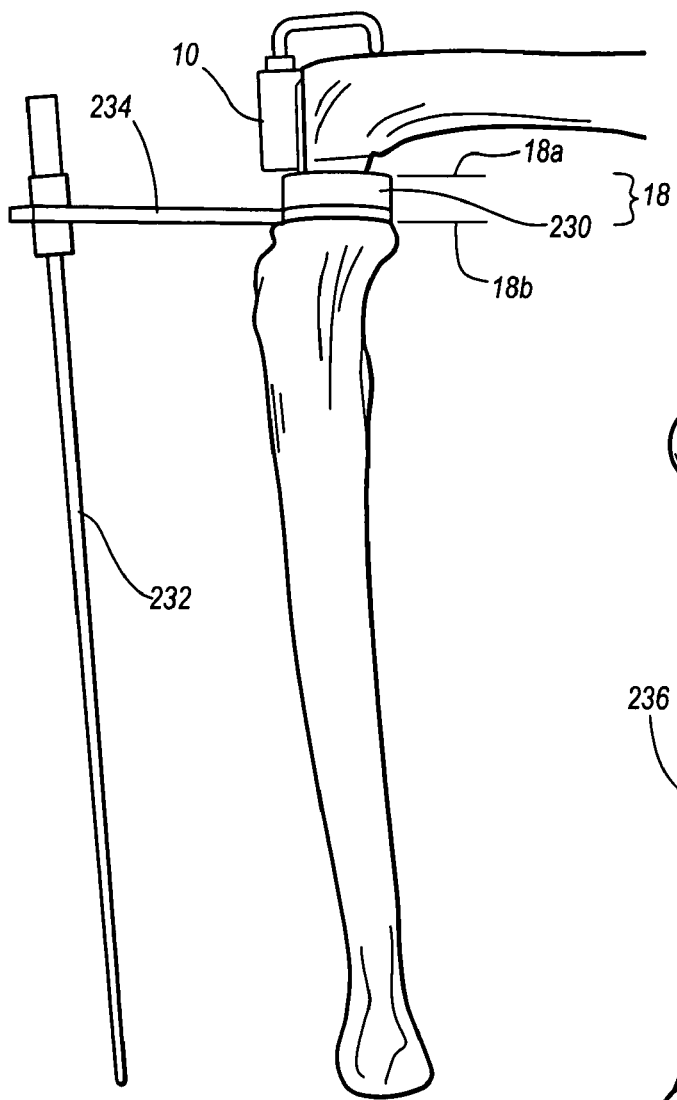
FIG. 17 is a side view of the A/P cutting guide device located on the distal end of the femur, illustrating the knee joint in flexion with a spacer block located in a flexion gap formed between the distal femur and the proximal tibia, with an alignment rod positioned for verifying appropriate alignment of the knee.

The posterior cut may now be made using standard cutting equipment, such as the oscillating saw mentioned above or another cutting instrument 350. After the posterior cut has been made, the A/P cutting guide device 10 and the quick pins 150 and 152 may be removed, and the spacer block 230 may then be used to determine equality of the flexion gap 18 and the extension gap 16, as illustrated in FIG. 17. If the flexion gap 18 is too tight, then the A/P cutting guide device 10 may be translated anteriorly, as described above, to accommodate the resection of more posterior distal femur, and thus increasing the flexion gap 18. If the flexion gap 18 is 4 mm too tight, then the option of downsizing to the next smaller femoral A/P cutting guide device 10 can be selected by the surgeon to increase the flexion gap 18. If the extension gap 16 is too tight, then resection of additional distal femoral bone will be performed to increase the extension gap 16. The final check may then be made using the spacer block 230 to ensure the flexion gap 18 is substantially equal to the extension gap 16. If it becomes necessary to make any adjustments after the check has been made, the A/P cutting guide device 10 may be placed back on the distal femur, and the device 10 rotated and/or translated until proper alignment has been achieved. At this point of the procedure, the extension gap 16 and the flexion gap 18 may both be substantially rectangular and equal in size.

Finally, the surgeon finishes the cutting procedure by making the rest of the femoral cuts, namely the anterior cut, and two chamfer cuts, and may then perform a trial reduction. The surgeon then proceeds with and finishes the remainder of the surgery.

Figure 18:
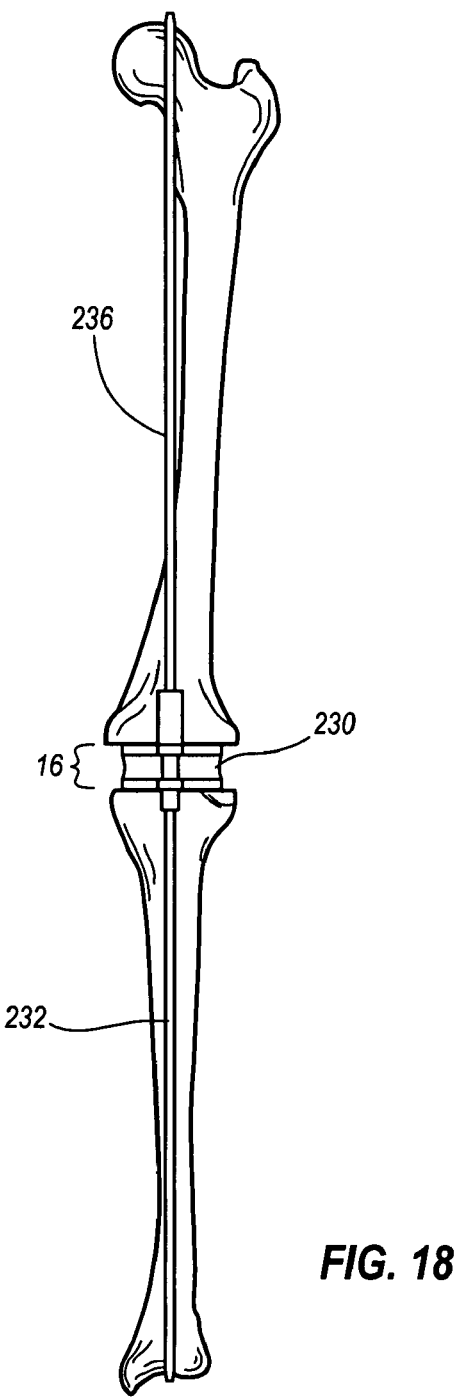
FIG. 18 is a back view of the spacer block located in an extension gap formed between the distal femur and the proximal tibia, illustrating the knee joint in extension with two alignment rods connected to the spacer block and positioned for assessing the overall alignment of the knee.

Additionally, as part of the foregoing procedure, a first alignment rod 232 may be attached to the spacer block 230 by way of a handle 234 and used to ensure that proper biomechanical alignment has been achieved as illustrated in FIG. 17. Additionally, the knee may be checked for proper alignment during extension using the same spacer block 230, and attaching a second alignment rod 236 to the first alignment rod 232 and also to the spacer block 230, as illustrated in FIG. 18.

It will be appreciated that the method and surgical steps referred to above may be accomplished using the unique features of the device 10. In accordance with the features and combinations described above, a useful method of surgically preparing a distal femur and a proximal tibia of a patient's knee joint to receive a prosthetic knee implant, comprises the steps of:

(a) exposing the patient's knee joint through a standard anterior midline incision;

(b) performing a distal femoral resection, including the steps of:

(i) drilling a hole in the distal femur to access a medullary canal in the femur, said hole designed to parallel a femoral shaft of the femur in an anterolateral direction and a mediolateral direction;

(ii) inserting a fluted T-handle through the opening and into the medullary canal to decompress marrow content in the medullary canal, removing the T-handle from said medullary canal, sliding said T-handle through an intramedullary alignment guide forming a first assembly, setting the alignment guide at an appropriate valgus angle, and inserting the first assembly into the medullary canal such that the alignment guide contacts a prominent most femoral condyle to thereby align the T-handle and alignment guide with said medullary canal;

(iii) assembling a distal femoral cut guide to a cut guide scaffolding forming a second assembly and inserting the second assembly into the alignment guide until the distal femoral cut guide contacts an anterior cortex of the femoral condyles;

(iv) adjusting an amount of distal femur to be resected, and fixing the distal femoral cut guide to the anterior cortex;

(v) removing the T-handle, alignment guide, and cut guide scaffolding from the distal femur leaving only the distal femoral cut guide; and (vi) resecting the amount of distal femur using a cutting instrument;

(c) performing a proximal tibial resection, including the steps of:

(i) positioning a tibial alignment guide having a top and a bottom on the patient's lower leg, positioning a tibial cut guide on the top of the tibial alignment guide, placing a tibial stylus on the tibial cut guide and adjusting the tibial stylus to a desired resection depth, and lowering the tibial cut guide onto the tibia until the tibial stylus contacts a tibial plateau;

(ii) fixing the tibial cut guide to the proximal tibia and removing the tibial stylus; and (iii) resecting the tibial plateau using a cutting instrument such that the resection is substantially perpendicular to a tibial shaft;

(d) balancing an extension gap, including the steps of:
  (i) placing a spacer block within the extension gap to check said extension gap;
  (ii) determining whether the extension gap is substantially rectangular in shape; and
  (iii) adjusting the length of the patient's ligaments using a series of ligament releases until the extension gap is substantially rectangular in shape;
(e) sizing the prosthetic femoral component with the patient's knee in flexion, including the steps of:
  (i) positioning a sizing guide having a femoral stylus and a paddle by centering said sizing guide on a surface of the distal femoral resection such that the femoral stylus of the sizing guide contacts the anterior cortex of the femur, and compressing the sizing guide until the paddle contacts at least one of the femoral condyles posteriorly; and
  (ii) reading a marking on the sizing guide corresponding to the appropriate size prosthetic femoral component, placing a plurality of securing members through the sizing guide and into the distal femoral resected surface, and removing said sizing guide from the plurality of securing members;
(f) locating an appropriately sized cutting guide device on the surface of the distal femoral resection, said device comprising a cut guide member, a support member, a positioning member, and a plurality of attachment members, including the steps of:
  (i) positioning the cut guide member, the support member and the positioning member over the plurality of securing members such that the support member may be anchored to the distal femur via the plurality of securing members, and such that the positioning member may be releasably secured to said support member, and the cut guide member may be releasably secured to said positioning member; and
  (ii) evaluating a potential flexion gap located between the distal femur and the proximal tibia prior to resecting a posterior portion of the distal femur to thereby determine if the cutting guide device is mal-aligned;
(g) adjusting the cutting guide device without removing any of the plurality of securing members in a rotational manner by loosening at least one of the plurality of attachment members thereby releasing the positioning member and the cut guide member from the support member such that the positioning member and the cut guide member rotate together about the plurality of securing members thereby rotating said cutting guide device, and thereafter tightening said at least one of the plurality of attachment members such that the flexion gap may be created in a substantially parallel manner;
(h) checking the flexion gap with said spacer block prior to resecting the posterior portion of the distal femur to verify that the flexion gap is substantially equal to the extension gap;
(i) adjusting the cutting guide device without removing any of the plurality of securing members in a translational manner, if necessary, by loosening at least one of the plurality of attachment members thereby releasing the cut guide member from the positioning member and the support member such that the cut guide member may move in an anterior direction and in a posterior direction, relative to said plurality of securing members, and thereafter tightening said at least one of the plurality of attachment members such that the flexion gap may be increased or decreased to substantially equal the size of the extension gap;
(j) performing a posterior distal femoral resection on a posterior side of said distal femur creating said flexion gap, and thereafter removing all instrumentation;
(k) checking said flexion gap with said spacer block to ensure an upper side of the flexion gap is substantially parallel with a lower side of said flexion gap, and to ensure that the flexion gap is substantially equal to the extension gap, and to further ensure that there is a desired fit between the spacer block, the femur and the tibia when said spacer block is seated in said flexion gap, and if necessary, adding the necessary instrumentation to the plurality of securing members and re-rotating and re-translating the instrumentation accordingly and making any additional cuts that may be necessary until the desired fit is obtained;
(l) performing a series of chamfer resections in the femur and otherwise preparing the tibia to thereby prepare said femur and said tibia to receive the prosthetic femoral component and the prosthetic tibial component, respectively, such that the patient's knee joint may be replaced;
(m) performing a trial reduction; and
(n) attaching the prosthetic femoral component and prosthetic tibial component to their respective bones and otherwise finishing the surgical procedure.

It will be appreciated that the structure and apparatus disclosed herein is merely one example of a means for attaching the cut guide member 20 to the support member 40, and it should be appreciated that any structure, apparatus or system for attaching the cut guide member 20 to the support member 40 which performs functions the same as, or equivalent to, those disclosed herein are intended to fall within the scope of a means for attaching, including those structures, apparatus or systems for attaching the cut guide member 20 to the support member 40 which are presently known, or which may become available in the future. Anything which functions the same as, or equivalently to, a means for attaching falls within the scope of this element.

It will also be appreciated that the structure and apparatus disclosed herein is merely one example of a means for rotating the cut guide member 20 and the means for attaching, and it should be appreciated that any structure, apparatus or system for rotating the cut guide member 20 and the means for attaching which performs functions the same as, or equivalent to, those disclosed herein are intended to fall within the scope of a means for rotating, including those structures, apparatus or systems for rotating which are presently known, or which may become available in the future. Anything which functions the same as, or equivalently to, a means for rotating falls within the scope of this element.

It will be appreciated that the structure and apparatus disclosed herein is merely one example of a means for translating the device 10, and it should be appreciated that any structure, apparatus or system for translating the device 10 which performs functions the same as, or equivalent to, those disclosed herein are intended to fall within the scope of a means for translating, including those structures, apparatus or systems for translating the device 10 which are presently known, or which may become available in the future. Anything which functions the same as, or equivalently to, a means for translating falls within the scope of this element.

Those having ordinary skill in the relevant art will appreciate the advantages provided by the features of the present invention. For example, after pinning the A/P cutting guide device 10 to the distal femur, the positioning member 30 may be released from the support member 40, permitting the positioning member 30 and the cut guide member 20 to move together in a rotational manner relative to the support member, which has been fixed to the quick pins 150 and 152, without removing the quick pins 150 and 152 from the distal femur. It is another potential feature of the present invention to enable the cut guide member 20 to move in a translational manner in the anterior/posterior direction relative to the support member 40, which has been fixed to the quick pins 150 and 152, without removing the quick pins 150 and 152 from the distal femur.

It is another potential feature of the present invention to provide an orthopedic A/P cutting guide device 10 which is simple in design and manufacture. Another potential feature of the present invention is to provide such an A/P cutting guide device 10 that is capable of correcting the rotational position of the device 10 on the distal femur after the device has been pinned to said distal femur. It is a further potential feature of the present invention to provide such an A/P cutting guide device 10 that is capable of correcting the translational positioning of the device 10 in the anterior/posterior direction on the distal femur. It is another potential feature of the present invention to provide a useful method that increases the ease and effectiveness of surgically resecting the posterior portion of the distal femur such that the flexion gap may be substantially equivalent to the extension gap, and provide for proper balancing of the ligaments in the knee joint.

It is to be understood that the above-described arrangements are only illustrative of the application of the principles of the present invention. Numerous modifications and alternative arrangements may be devised by those skilled in the art without departing from the spirit and scope of the present invention and the patent claims are intended to cover such modifications and arrangements. Thus, while the present invention has been shown in the drawings and described above with particularity and detail, it will be apparent to those of ordinary skill in the art that numerous modifications, including, but not limited to, variations in size, materials, shape, form, function and manner of operation, assembly and use may be made without departing from the principles and concepts set forth herein.

What is claimed is:

1. An orthopedic cutting guide device for use in resecting a portion of a bone, the device comprising:
    a first member having a pivot, and configured to be anchored to the bone;
    a second member releasably secured to the first member; and
    a cut guide member releasably secured directly to the second member such that the first member is positioned in between the cut guide member and the second member and such that the cut guide member and the second member move together about the pivot of the first member when said second member is selectively released from said first member, wherein said cut guide member is further secured to said second member such that when the cut guide member is selectively released from said second member the cut guide member is thereby permitted to move with respect to said first member independently from said second member;
    wherein the orthopedic cutting guide device is configured to be selectively adjusted in both a rotational and translational manner while the first member is anchored to the bone;
    wherein said device further comprises at least one securing member adapted to be implanted within and protrude from the bone; and
    wherein said first member comprises at least one through hole dimensioned for permitting the at least one securing member to pass therethrough.

2. The orthopedic cutting guide device of claim 1, wherein the first member is adapted to be anchored to the bone by the at least one securing member.

3. The orthopedic cutting guide device of claim 1, wherein said device further comprises a boom configured as a reference to aid the surgeon in making an anterior cut in the bone, and further aids in the avoidance of notching the bone.

4. The orthopedic cutting guide device of claim 3, wherein the cut guide member comprises a top surface and a bottom surface, said top surface having an opening therein configured for receiving a portion of the boom.

5. The orthopedic cutting guide device of claim 4, wherein the boom comprises a first end and a second end, the first end of said boom being dimensioned to fit within the opening of the cut guide member and configured and dimensioned to be secured therein.

6. The orthopedic cutting guide device of claim 1, wherein said first member comprises a top surface, a bottom surface, an outer wall, a first end and a second end, said outer wall tapering outwardly from a central reference point toward the first end and the second end.

7. The orthopedic cutting guide device of claim 6, wherein said first end and said second end of said first member each act as the pivot, and are each shaped in a substantially rounded configuration.

8. The orthopedic cutting guide device of claim 7, wherein the tapering of the outer wall of the first member results in a height measured between the top surface and the bottom surface at the central reference point that is greater than a height measured between the top surface and bottom surface at the first end and the second end.

9. The orthopedic cutting guide device of claim 1, wherein said first member comprises a central through hole.

10. The orthopedic cutting guide device of claim 1, wherein said first member comprises a central through hole, a first side and a second side, wherein the first side and the second side each comprise a plurality of protrusions located medially and laterally of the central through hole of the first member for interacting with the second member and the cut guide member.

11. The orthopedic cutting guide device of claim 10, wherein said cut guide member further comprises a plurality of substantially elongated holes configured for interacting with at least one of the plurality of protrusions.

12. The orthopedic cutting guide device of claim 10, wherein said second member comprises a plurality of through holes, and said cut guide member comprises a plurality of through holes, such that the plurality of protrusions of the first side of the first member are inserted into the plurality of through holes of the second member, and the plurality of protrusions of the second side of the first member are inserted into plurality of through holes of the cut guide member, to thereby interact with one another during adjustment of the device.

13. The orthopedic cutting guide device of claim 1, wherein said second member comprises a plurality of through holes.

14. The orthopedic cutting guide device of claim 13, wherein the plurality of through holes comprises a central hole, a plurality of translational through holes, and a plurality of through holes located medially and laterally of said central through hole.

15. The orthopedic cutting guide device of claim 1, wherein said second member comprises a central through hole and at least one through hole located on either side of the central through hole.

16. The orthopedic cutting guide device of claim 15, wherein the at least one through hole is shaped in a substantially arcuate manner.

17. The orthopedic cutting guide device of claim 1, wherein said second member comprises at least one translational through hole.

18. The orthopedic cutting guide device of claim 17, wherein said second member comprises a first end and a second end, and wherein said at least one translational through hole comprises a plurality of translational through holes, and wherein at least one of the plurality of translational through holes is located near each of the first end and the second end of the second member.

19. The orthopedic cutting guide device of claim 17, wherein said at least one translational through hole comprises a substantially elongated shape.

20. The orthopedic cutting guide device of claim 1, wherein said second member comprises a first protruding wall and a second protruding wall.

21. The orthopedic cutting guide device of claim 20, wherein said second member further comprises a first side and a second side, wherein said first protruding wall and said second protruding wall both protrude outwardly from the second side of the second member in a substantially orthogonal manner.

22. The orthopedic cutting guide device of claim 21, wherein said first protruding wall and said second protruding wall are shaped in a substantially arcuate manner.

23. The orthopedic cutting guide device of claim 1, wherein said second member comprises a series of markings corresponding to a predetermined angle of rotation of the second member.

24. The orthopedic cutting guide device of claim 1, wherein said cut guide member further comprises a recessed surface and a sidewall defining a recessed area.

25. The orthopedic cutting guide device of claim 1, wherein said cut guide member further comprises an anterior portion and a posterior portion, said anterior portion having an anterior cutting guide and said posterior portion having a posterior cutting guide.

26. The orthopedic cutting guide device of claim 25, wherein said cut guide member further comprises a connecting portion located on the anterior side of the cut guide member, said connecting portion comprising an opening for receiving a boom therein.

27. The orthopedic cutting guide device of claim 1, wherein said cut guide member further comprises a plurality of receiving holes, each receiving hole configured for receiving an attachment member therein.

28. The orthopedic cutting guide device of claim 1, wherein the device further comprises an attachment member configured for releasably securing the second member to the first member, whereby the surgeon selectively loosens the attachment member thereby releasing said second member from the first member such that the second member and the cut guide member rotate together about the pivot of the first member.

29. The orthopedic cutting guide device of claim 1, wherein the device further comprises at least one attachment member configured for releasably securing the cut guide member to the second member, whereby the surgeon selectively loosens the at least one attachment member thereby releasing the cut guide member from the second member such that the cut guide member moves in said translational manner independent from both the second member and the first member.

30. The orthopedic cutting guide device of claim 1, wherein the cut guide member further comprises an anterior cutting guide formed in an anterior portion of said cut guide member.

31. The orthopedic cutting guide device of claim 30, wherein the anterior cutting guide slopes downwardly in a proximal to distal direction from a back surface to a front surface of the cut guide member such that a resulting anterior cut is tapered.

32. The orthopedic cutting guide device of claim 30, wherein the anterior cutting guide is formed as a slit in the anterior portion of said cut guide member.

33. The orthopedic cutting guide device of claim 1, wherein the cut guide member further comprises a posterior portion having a posterior cutting guide that is configured and dimensioned as a template for making a posterior cut in the bone.

34. The orthopedic cutting guide device of claim 33, wherein the posterior cutting guide comprises a substantially flat surface that enables a surgeon to place a cutting instrument in contact with the substantially flat surface of said posterior cutting guide, such that a cut that is substantially straight and flat can be made.

35. The orthopedic cutting guide device of claim 33, wherein the posterior cutting guide is a bottom edge of the cut guide member.

36. An orthopedic cutting guide device for use in resecting a portion of a bone, the device comprising:
a first member having a pivot, and configured to be anchored to the bone;
a second member releasably secured to the first member; and
a cut guide member releasably secured directly to the second member such that the first member is positioned in between the cut guide member and the second member and such that the cut guide member and the second member move together about the pivot of the first member when said second member is selectively released from said first member, wherein said cut guide member is further secured to said second member such that when the cut guide member is selectively released from said second member the cut guide member is thereby permitted to move with respect to said first member independently from said second member;
wherein the orthopedic cutting guide device is configured to be selectively adjusted in both a rotational and translational manner while the first member is anchored to the bone; and
wherein said second member comprises a plurality of through holes.

37. An orthopedic cutting guide device for use in resecting a portion of a bone, the device comprising:
a first member having a pivot, and configured to be anchored to the bone;
a second member releasably secured to the first member; and
a cut guide member releasably secured directly to the second member such that the first member is positioned in between the cut guide member and the second member and such that the cut guide member and the second member move together about the pivot of the first member when said second member is selectively released from said first member, wherein said cut guide member is further secured to said second member such that when the cut guide member is selectively released from said second member the cut guide member is thereby permitted to move with respect to said first member independently from said second member;

wherein the orthopedic cutting guide device is configured to be selectively adjusted in both a rotational and translational manner while the first member is anchored to the bone; and wherein said second member comprises at least one translational through hole.

38. An orthopedic cutting guide device for use in resecting a portion of a bone, the device comprising:
- a first member having a pivot, and configured to be anchored to the bone;
- a second member releasably secured to the first member; and
- a cut guide member releasably secured directly to the second member such that the first member is positioned in between the cut guide member and the second member and such that the cut guide member and the second member move together about the pivot of the first member when said second member is selectively released from said first member, wherein said cut guide member is further secured to said second member such that when the cut guide member is selectively released from said second member the cut guide member is thereby permitted to move with respect to said first member independently from said second member;
- wherein the orthopedic cutting guide device is configured to be selectively adjusted in both a rotational and translational manner while the first member is anchored to the bone; and
- wherein said second member comprises a first protruding wall and a second protruding wall.

39. An orthopedic cutting guide device for use in resecting a portion of a bone, the device comprising:
- a first member having a pivot, and configured to be anchored to the bone;
- a second member releasably secured to the first member; and
- a cut guide member releasably secured directly to the second member such that the first member is positioned in between the cut guide member and the second member and such that the cut guide member and the second member move together about the pivot of the first member when said second member is selectively released from said first member, wherein said cut guide member is further secured to said second member such that when the cut guide member is selectively released from said second member the cut guide member is thereby permitted to move with respect to said first member independently from said second member;
- wherein the orthopedic cutting guide device is configured to be selectively adjusted in both a rotational and translational manner while the first member is anchored to the bone; and
- wherein the device further comprises an attachment member configured for releasably securing the second member to the first member, whereby the surgeon selectively loosens the attachment member thereby releasing said second member from the first member such that the second member and the cut guide member rotate together about the pivot of the first member.

40. An orthopedic cutting guide device for use in resecting a portion of a bone, the device comprising:
- a first member having a pivot, and configured to be anchored to the bone;
- a second member releasably secured to the first member; and
- a cut guide member releasably secured directly to the second member such that the first member is positioned in between the cut guide member and the second member and such that the cut guide member and the second member move together about the pivot of the first member when said second member is selectively released from said first member, wherein said cut guide member is further secured to said second member such that when the cut guide member is selectively released from said second member the cut guide member is thereby permitted to move with respect to said first member independently from said second member;
- wherein the orthopedic cutting guide device is configured to be selectively adjusted in both a rotational and translational manner while the first member is anchored to the bone; and
- wherein the device further comprises at least one attachment member configured for releasably securing the cut guide member to the second member, whereby the surgeon selectively loosens the at least one attachment member thereby releasing the cut guide member from the second member such that the cut guide member moves in said translational manner independent from both the second member and the first member.

* * * * *

UNITED STATES PATENT AND TRADEMARK OFFICE
CERTIFICATE OF CORRECTION

| | | |
|---|---|---|
| PATENT NO. | : 7,628,793 B2 | Page 1 of 1 |
| APPLICATION NO. | : 10/618521 | |
| DATED | : December 8, 2009 | |
| INVENTOR(S) | : Calton et al. | |

It is certified that error appears in the above-identified patent and that said Letters Patent is hereby corrected as shown below:

On the Title Page:

The first or sole Notice should read --

Subject to any disclaimer, the term of this patent is extended or adjusted under 35 U.S.C. 154(b) by 1805 days.

Signed and Sealed this

Second Day of November, 2010

David J. Kappos
*Director of the United States Patent and Trademark Office*